United States Patent
Nanjo et al.

(10) Patent No.: US 8,128,802 B2
(45) Date of Patent: Mar. 6, 2012

(54) ANALYSIS APPARATUS AND ANALYSIS METHOD FOR GLYCOSYLATED HEMOGLOBIN

(75) Inventors: Yoko Nanjo, Amagasaki (JP); Ryuzo Hayashi, Amagasaki (JP)

(73) Assignees: OJI Paper Co., Ltd, Tokyo (JP); OJI Scientific Instruments Co., Ltd, Hyogo (JP)

( * ) Notice: Subject to any disclaimer, the term of this patent is extended or adjusted under 35 U.S.C. 154(b) by 1157 days.

(21) Appl. No.: 11/913,367

(22) PCT Filed: May 2, 2006

(86) PCT No.: PCT/JP2006/309172
§ 371 (c)(1),
(2), (4) Date: Nov. 1, 2007

(87) PCT Pub. No.: WO2006/118306
PCT Pub. Date: Nov. 9, 2006

(65) Prior Publication Data
US 2008/0223733 A1 Sep. 18, 2008

(30) Foreign Application Priority Data

| May 2, 2005 | (JP) | 2005-134591 |
| Nov. 15, 2005 | (JP) | 2005-330338 |
| Dec. 8, 2005 | (JP) | 2005-355450 |

(51) Int. Cl.
*G01N 27/327* (2006.01)
(52) U.S. Cl. .......... 205/777.5; 204/403.14
(58) Field of Classification Search ........... 204/403.01–403.15, 409–412; 205/777.5, 778, 792
See application file for complete search history.

(56) References Cited

U.S. PATENT DOCUMENTS
| 2006/0148096 A1* | 7/2006 | Jina .................... 436/514 |
| 2007/0178547 A1 | 8/2007 | Taniguchi et al. |

FOREIGN PATENT DOCUMENTS
| EP | 1614746 A | | 1/2006 |
| JP | 02-159563 A | * | 6/1990 |
| JP | 05-033997 | | 5/1993 |
| JP | 05-059380 | | 8/1993 |
| JP | 08-154672 | | 6/1996 |
| JP | 2000-333696 | | 12/2000 |
| JP | 2001-095598 | | 4/2001 |
| JP | 2001-215229 | | 8/2001 |
| JP | 2003-235585 | | 8/2003 |
| JP | 2003-274976 | | 9/2003 |
| JP | 2004-275013 | | 10/2004 |
| JP | 2004-344052 | | 12/2004 |

(Continued)

OTHER PUBLICATIONS
JPO computer generated English language translation of JP 2003-121410 A, downloaded Jul. 16, 2011.*

(Continued)

*Primary Examiner* — Alex Noguerola
(74) *Attorney, Agent, or Firm* — Sughrue Mion, PLLC

(57) ABSTRACT

Disclosed is a method for calculating a ratio of glycosylated hemoglobin with high accuracy by electrochemically detecting the concentration of fructosyl valine or fructosyl valyl-histidine in a sample. Also disclosed is an apparatus for assaying glucose and glycosylated hemoglobin simultaneously. Further disclosed are a method and an apparatus for removing hydrogen peroxide in a sample.

11 Claims, 5 Drawing Sheets

FOREIGN PATENT DOCUMENTS

| | | |
|---|---|---|
| JP | 2005-110657 | 4/2005 |
| WO | 2004083149 A1 | 9/2004 |
| WO | 2005/087946 A1 | 9/2005 |

OTHER PUBLICATIONS

JPO computer generated English language translation of JP 2003-322635 A, downloaded Jul. 16, 2011.*

JPO computer generated English language translation of JP 08-271478 A, downloaded Jul. 16, 2011.*

JPO computer generated English language translation of the abstract of JP 02-159563 A, downloaded Jul. 16, 2011.*

Full English language transaltion of Yoshio Watanabe et al. JP 02159563 A, translated Aug. 2011.*

Official Communication dated Oct. 19, 2009, issued in European Patent Application No. 06746022.0.

Japanese Office Action dated May 19, 2010, as issued in Japanese Patent Application No. 2005-330338.

Hirokawa et al, *Biotechnol. Lett.*, 27(14):963-968 (2005).

Tsugawa et al, *Electrochemistry*, 68(11):869-871 (2000).

Tsugawa et al, *Electrochemistry*, 69(12):973-975 (2001).

Ogawa et al, *Anal. Bioanal. Chem.*, 373(4-5):211-214 (2002).

Sakaguchi et al, *Electrochemistry*, 71(6):442-445 (2003).

Sakurabayashi et al, *Clin. Chem.*, 49(2):269-274 (2003).

Hirokawa et al, *FEMS Microbiol. Lett.*, 235(1):157-162 (2004).

Hirokawa et al, *Biochem. Biophys. Res. Commun.*, 311(1):104-111 (2003).

* cited by examiner

ANALYSIS APPARATUS AND ANALYSIS METHOD FOR GLYCOSYLATED HEMOGLOBIN

TECHNICAL FIELD

The present invention relates to an apparatus and a method for assaying a ratio of glycohemoglobin with high speed and high accuracy, which contributes to health management and clinical diagnosis.

BACKGROUND ART

Glycohemoglobin is widely used as an indicator of a long-term glycemic control in diabetic patients. Glycohemoglobin in which glucose is nonenzymatically attached to hemoglobin is one of the glycated proteins. Among glycohemoglobin, particularly a fraction referred to as HbA1c is produced by binding glucose to an N-terminal valine residue of the β-chain in hemoglobin A to form a Schiff base aldimine (labile form) and then undergoing Amadori rearrangement to form a ketoamine. Glycohemoglobin with an aldimine structure is referred to as labile glycohemoglobin, whereas glycohemoglobin with a ketoamine structure is referred to as stable glycohemoglobin. After the Amadori rearrangement, the N-terminal of the β-chain becomes a fructosyl valine residue.

No enzyme is involved in this process, and its amount is increased depending on a glucose concentration in plasma. When so-called a blood glucose concentration in plasma is high in average for a long time, the HbA1c value becomes high. The stable glycohemoglobin does not disappear until a life span of an erythrocyte is terminated. It is generally known that the life span of a hemoglobin molecule in vivo is about 2 months, and that as a result, the HbA1c value reflects the average blood glucose concentration during the past one to two months. Thus, the HbA1c value is used as the indicator of the average blood glucose concentration over a long period of time. Generally, the blood glucose concentration changes easily, depending on the lifestyle type and diet before the diagnosis examination. However, the HbA1c value is the average value for a long time, and thus is suitable for using as information for making a decision for a definite diagnosis and a therapy of diabetes.

Thus, many of the various methods for assaying glycohemoglobin have been already proposed. As their representatives, high performance liquid chromatography (HPLC) methods, immunoassays and enzymatic assays are included.

The HPLC method is most frequently used at present. Hemoglobin is fractionated on a separation column, and a so-called area normalization method in which an abundance ratio of HbA1c is calculated from a peak area of an elution at a retention volume corresponding to HbA1c and a total peak area is employed. Thus, it is advantageous in that an accuracy of an injected volume can be ignored to some extent. However, it includes problems in that the apparatus is large and complicated, and its maintenance is time-consuming. Also, it has faults that the separation and measurement must be performed after previously removing labile HbA1c because labile HbA1c and stable HbA1c can not be distinguished (Patent Document 1). Furthermore, because of hemoglobin variants, a separation pattern occasionally varies to produce an abnormal value. It is also likely that obtained HbA1c value has errors because other biocomponents are accidentally overlapped with the peak of HbA1c.

The immunoassay has a possibility that the higher accurate determination is accomplished by a simpler system by taking advantage of an antibody against the structure in the vicinity of the N-terminus of the β-chain in HbA1c. However, differently from the general immunoassays, a sample hemolyzing whole blood is used instead of serum. Thus, nonspecific reactions easily occur and a calorimeter for the detection of the reaction is easily contaminated. Accordingly, it has been disclosed that satisfactory results are not always obtained.

Meanwhile, in the enzyme assays, a fructosyl peptide or a fructosyl amino acid is produced from the glycated protein by some means, and the resulting fructosyl peptide or fructosyl amino acid is detected and quantified using an enzyme such as fructosyl peptide oxidase or fructosyl amino acid oxidase. It is likely possible to carried out the higher accurate determination by taking advantage of the selectivity in the enzyme.

First, the means for determining the fructosyl amino acid by the enzyme is described in Patent Document 2, but the means for producing the fructosyl amino acid from the glycated protein is not described.

In addition, there are still many problems to be solved.

First, a protease which produces the fructosyl peptide or the fructosyl amino acid as rapidly as possible is required. At the same time, the protease with high activity likely digests not only hemoglobin but also fructosyl peptide oxidase and fructosyl amino acid oxidase. Thus, the method for the selective digestion of hemoglobin has been sought, but no effective method has been found yet.

Second, the N-terminal amino acids in both of the α-chain and the β-chain in hemoglobin are valine residues, and in the case of detecting the fructosyl amino acid, it is desirable that the protease which librates the fructosyl amino acid ideally acts upon only the β-chain. However, no protease with the high selectivity for extremely similar substrates such as the α-chain and the β-chain has been found yet.

From another standpoint, a solution has been proposed for this problem. That is, the fructosyl amino acid librated by the protease is not detected, and the glycated a chain and the glycated β chain are distinguished by detecting the fructosyl dipeptide or the fructosyl peptide. Particularly, an oxidase which selectively acts upon fructosyl valylhistidine in fructosyl dipeptides is proposed (Patent Documents 3, 4 and 5). By taking advantage of fructosyl peptide oxidase, which acts upon the fructosyl valylhistidine, it is possible to decrease requirements for the substrate specificity in the protease.

However, in Patent Document 3, the means for determining the glycated protein by measuring a sample digested with the protease using fructosyl peptide oxidase or HPLC has been disclosed. However, another specificity that the protease acts upon only the glycated protein and does not act upon fructosyl peptide oxidase has not been investigated. Even in Examples, only an example in which the protease is inactivated in heat and subjected to ultrafiltration is described.

In Patent Document 4, an enzyme activity is assayed using standard substrates of a low molecular weight, and the means for librating the fructosyl peptide from the glycated protein is not disclosed.

In Patent Document 5, the method for the determination of HbA1c by measuring the fructosyl peptide in the glycohemoglobin using the extremely excessive protease from *Streptomyces* sp. is exemplified. However, as described in Patent Document 5, many fructosyl peptide oxidases also have the ability to act upon fructosyl amino acid. Therefore, in the presence of extremely excessive protease, it is not clear which of the fructosyl peptide or the fructosyl amino acid is acted upon, and there is no example in which the specificity for the hemoglobin β-chain characteristic for fructosyl peptide oxidase has been completely exerted.

In Patent Document 6, the combination of the enzyme which acts upon the fructosyl peptide or the fructosyl amino acid to produce hydrogen peroxide with the protease producing its substrate was investigated. In this patent, the activity of the protease to produce the fructosyl amino acid is evaluated as the activity to liberate the fructosyl amino acid from the fructosyl dipeptide. The activity to produce the fructosyl dipeptide is evaluated as the activity to liberate a nitroaniline derivative from a nitroanilide derivative of the fructosyl dipeptide. Therefore, it is not clear whether the fructosyl peptide or the fructosyl amino acid is actually librated from glycated protein with high molecular weight, particularly glycohemoglobin. In fact, the inventors of the present application could not confirm the effectiveness of papain which was the protease from a plant and had been described to be effective in this invention.

In Patent Document 7, as the means for librating the fructosyl dipeptide, various proteases are exemplified, but actually, the means for librating fructosyl dipeptide from fructosyl hexapeptide has been investigated, and glycohemoglobin has not been digested. In a replication study by the inventor of the present application, no response was observed at all in the proteases, particularly papain and the protease from *Aspergillus* sp. except one from *Bacillus* sp., and the response was observed only in the protease from *Bacillus* sp. It was indicated that the replication study was not effected. A reason for this is not clear, but it is suggested that another product produced simultaneously with fructosyl valylhistidine by the proteolysis is detected in Patent Document 7.

When glycohemoglobin is consistently measured, it is necessary that the substrate used for the screening of the protease is hemoglobin itself. When a protease is utilized, it is desirable to detect only the fructosyl peptide. However, conventionally, the means for efficiently digesting glycohemoglobin and detecting only the required fructosyl peptide has not been disclosed.

Furthermore, no method and no apparatus which detects the total amount of hemoglobin in the sample and calculates the ratio of glycohemoglobin simply and accurately have been disclosed.

Patent Document 1: JP Hei-05-59380-B
Patent Document 2: JP Hei-05-33997-B
Patent Document 3: JP 2001-95598-A
Patent Document 4: JP 2003-235585-A
Patent Document 5: JP 2004-275013-A
Patent Document 6: JP 2004-344052-A
Patent Document 7: JP 2005-110657-A

DISCLOSURE OF THE INVENTION

Problems to be Solved by the Invention

It is an object of the present invention to provide a method for determining an amount of glycohemoglobin with high accuracy.

It is another object of the present invention to provide a method and an apparatus for using an immobilized enzyme of fructosyl peptide oxidase specific for a fructosyl dipeptide produced from glycohemoglobin or an immobilized enzyme of fructosyl amino acid oxidase specific for a fructosyl amino acid produced from the glycohemoglobin, and to enable an accurate quantification of a glycated β-chain in hemoglobin defined as HbA1c.

It is a further object of the present invention to provide an apparatus which is simply and highly accurately calculating a blood glucose concentration and a ratio of glycohemoglobin in a sample.

It is one more object of the present invention to provide a protease capable of the efficient digestion of glycohemoglobin.

It is a further object of the present invention to provide a method and an apparatus which simply and accurately detects the total amount of hemoglobin contained in a sample and calculates a ratio of glycohemoglobin.

Means for Solving the Problems

The present invention relates to an apparatus for assaying glycohemoglobin characterized by having an immobilized enzyme (17) in which either fructosyl peptide oxidase which acts upon fructosyl L-valylhistidine or fructosyl L-amino acid oxidase which acts upon fructosyl L-valine has been immobilized and an electrochemical detector (18) to detect electroactive components which are produced or consumed by a catalytic reaction of immobilized enzyme of the oxidase, and comprising a machinery (4, 5, 7) to contact a sample containing glycohemoglobin with a protease for a certain time and inject a part thereof.

The present invention discloses an apparatus for assaying glycohemoglobin characterized by comprising an immobilized enzyme (17) in which either fructosyl peptide oxidase which acts upon fructosyl L-valylhistidine or fructosyl L-amino acid oxidase which acts upon fructosyl L-valine has been immobilized and an electrochemical detector (18) to detect electroactive components which are produced or consumed by a catalytic reaction of immobilized enzyme of the oxidase and a machinery (4, 5, 7) to inject a sample containing glycohemoglobin, and comprising a column reactor immobilized a protease downstream of the sample injection machinery.

Furthermore, the present invention discloses an apparatus for assaying glycohemoglobin comprising an immobilized enzyme (17) in which either fructosyl peptide oxidase, which acts upon fructosyl L-valylhistidine, or fructosyl L-amino acid oxidase, which acts upon fructosyl L-valine, has been immobilized and an electrochemical detector (18) to detect electroactive components, which are produced or consumed by catalytic reaction of immobilized enzymes of the oxidase, and machinery (4, 5, 7) to inject a sample containing glycohemoglobin, and comprising a system to calculate a hemoglobin amount from an absorbance of the sample and calculate a ratio of glycohemoglobin from the hemoglobin amount and a fructosyl peptide amount or a fructosyl amino acid amount in or downstream of the sample injection machinery (4, 5, 7).

When fructosyl peptide oxidase which acts upon fructosyl valylhistidine is used, it is desirable that the protease contacted with the sample containing glycohemoglobin for a certain time is the neutral or acidic protease or variants thereof generated from *Bacillus subtilis*.

When fructosyl amino acid oxidase, which acts upon fructosyl valine, is used, it is desirable that the protease contacted with the sample containing glycohemoglobin for a certain time is the alkaline protease or variants thereof generated from *Aspergillus oryzae*.

Furthermore, the present invention discloses an apparatus for assaying glucose and glycohemoglobin comprising an immobilized enzyme which catalyzes an oxidation of glucose and a system to detect electroactive components which are produced or consumed by the oxidation of glucose, further comprising a system to detect electroactive components which are produced or consumed by the oxidation of fructosyl valylhistidine or fructosyl valine due to an immobilized enzyme of fructosyl peptide oxidase or fructosyl amino acid oxidase and a detection system of total hemoglobin, and comprising a first arithmetic system to obtain a ratio of glycohemoglobin based on a detected fructosyl valylhistidine or fructosyl valine and a detected hemoglobin and a second arithmetic system to correct glucose in whole blood into glucose in plasma based on detected whole blood glucose and hemoglobin.

Furthermore, the present invention also discloses an apparatus for assaying glucose and glycohemoglobin characterized by comprising an immobilized enzyme which catalyzes an oxidation of glucose, a system to detect electroactive components which are produced or consumed by the oxidation of glucose, an immobilized enzyme in which fructosyl L-amino acid oxidase, which acts upon fructosyl L-valine, has been immobilized, or an immobilized enzyme in which fructosyl peptide oxidase, which acts upon fructosyl L-valylhistidine, has been immobilized, and a machinery to detect electroactive components which are produced or consumed by the oxidative reaction of a fructosyl amino acid or a fructosyl peptide, a detection system of total hemoglobin, a third arithmetic system to obtain fructosyl valylhistidine amount or fructosyl valine amount with eliminating an interference from glucose in the sample based on the detected glucose and fructosyl valylhistidine in the sample or the detected glucose and fructosyl valine in the sample, a first arithmetic system to obtain a ratio of glycohemoglobin based on the detected fructosyl valylhistidine and hemoglobin or the detected fructosyl valine and hemoglobin, and a second arithmetic system to correct glucose in whole blood into glucose in plasma based on the detected whole blood glucose and hemoglobin.

The present invention also relates to a method for assaying glycohemoglobin characterized by pipetting a whole blood sample, which is then dispersed in a solution containing a surfactant to hemolyze, contacting a protease with the hemolyzate for a given time, determining a hemoglobin concentration by measuring an absorbance of a solution digested by the protease, as well as contacting a part of the digested solution with an immobilized enzyme in which either fructosyl peptide oxidase which acts upon fructosyl L-valylhistidine or fructosyl amino acid oxidase which acts upon fructosyl L-valine has been immobilized and an electrochemical detection of electroactive components which are produced or consumed by a reaction catalyzed by the oxidase.

Particularly, it is desirable that the surfactant is anionic with sulfone group.

Furthermore, the present invention discloses a method for assaying glucose and glycohemoglobin in the sample comprising the following:

a step of an electrochemical detection of a glucose concentration in the sample using an immobilized enzyme in which an enzyme which catalyzes the oxidation of glucose has been immobilized and an electrochemical detector of electroactive components which are produced and consumed by the oxidation of glucose;

a step of an electrochemical detection of fructosyl L-valine or fructosyl valylhistidine in the sample using an immobilized enzyme in which fructosyl amino acid oxidase which acts upon fructosyl L-valine has been immobilized or an immobilized enzyme in which fructosyl peptide oxidase which acts upon fructosyl L-valylhistidine has been immobilized, and an electrochemical detection of electroactive components which are produced or consumed by the oxidation of a fructosyl amino acid or a fructosyl peptide;

a step of detecting total hemoglobin in the sample using a detection system of total hemoglobin;

a step of obtaining HbA1c values by a first arithmetic system based on the detected fructosyl L-valine and hemoglobin or the detected fructosyl valylhistidine and hemoglobin; and a step of correcting glucose in whole blood/blood cell into glucose in plasma by a second arithmetic system based on the detected glucose in whole blood/blood cell and hemoglobin.

It is desirable that the method further comprises a step of obtaining a measurement value of fructosyl L-valine or fructosyl valylhistidine with eliminating the interference from glucose in the sample by a third arithmetic system based on the detected glucose and fructosyl L-valine in the sample or the detected glucose and fructosyl valylhistidine in the sample, and that HbA1c is obtained by the first arithmetic system based on the obtained measurement value and the detected hemoglobin.

Effects of the Invention

The present invention provides the simple and highly accurate determination of stable glycohemoglobin in the blood sample, and also the rapid determination of the blood glucose concentration and the ratio of glycohemoglobin.

Also the present invention provides the simple and highly accurate quantification of a glucose concentration in plasma and a ratio of glycohemoglobin (i.e., HbA1c) in the blood sample.

The apparatus of the present invention enables calculating the glucose concentration and a ratio of HbA1c simultaneously using the first and second arithmetic systems. In addition, the glucose concentration in the sample is corrected into the glucose concentration in plasma based on the hemoglobin concentration essential for the calculation of the ratio of HbA1c by the second arithmetic system, and the ratio of HbA1c is calculated by the second arithmetic system after the concentration of fructosyl L-valine or fructosyl valylhistidine eliminating the interference from glucose is obtained by the third arithmetic system. Thus glucose in plasma and the ratio of HbA1c can be measured efficiently and accurately.

EXPLANATIONS OF LETTERS

Figure 1:
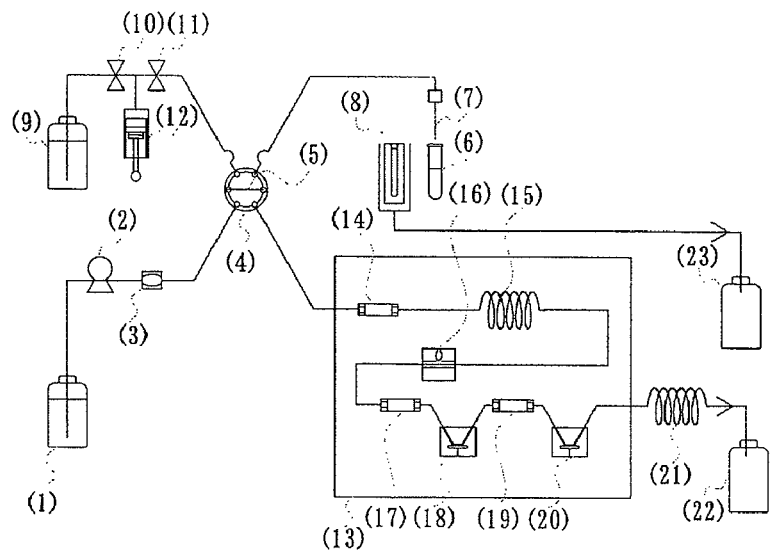
FIG. 1 shows a schematic assay apparatus.

1. Buffer tank
2. Buffer sending pump
3. Damper
4. Valve for injection of a constant volume
5. Sample loop
6. Sample tube
7. Sample pipetting needle
8. Waste pot
9. Washing solution tank
10. Valve
11. Valve
12. Syringe pump
13. Incubator
14. Protease-immobilized column
15. Mixing coil
16. Flow type colorimeter
17. First immobilized enzyme column
18. Electrode for hydrogen peroxide
19. Second immobilized enzyme column
20. Electrode for hydrogen peroxide
21. Back pressure coil
22. Waste tank
23. Waste tank
24. Buffer tank
25. Buffer sending pump
26. Coil for thermostabilization
27. Dialysis module

MODES FOR CARRYING OUT THE INVENTION

Herein, a sample includes whole blood or a blood cell, and the whole blood is preferable. In preferable concretes of the present invention, the sample is digested by a protease which produces either fructosyl valylhistidine or fructosyl valine.

In the available protease when fructosyl peptide oxidase is used in the present invention, it is preferable that an action to produce an N-terminal fructosyl peptide from glycohemoglobin or its fragment is large.

Likewise, in the available protease when fructosyl amino acid oxidase is used in the present invention, it is preferable that the action to produce an N-terminal fructosyl amino acid from glycohemoglobin or its fragment is large.

When fructosyl peptide oxidase is used, the large action is observed in the protease from *Bacillus* sp. When fructosyl amino acid oxidase is used, the large action is observed in the protease from *Aspergillus* sp., particularly protease from *Aspergillus oryzae*.

Human hemoglobin is precipitated at pH 5.0 or below. Thus, to allow the protease to act effectively, it is preferable that the protease has an optimal pH in the range at which hemoglobin can be thoroughly dissolved.

The protease, which produces fructosyl valylhistidine and is obtained from *Bacillus* sp. and has an acidic or neutral optimal range, has an optimum preferably at pH 6.0 to 10.0 and more preferably at pH 6.0 to 7.0. Specifically, Protease N (Amano Enzyme Inc.), Protin PC10F (Daiwa Kasei K.K.), Protamex (Novozyme) and Neutrase (Novozyme) can be exemplified. In addition to these proteases from *Bacillus* sp., the proteases from *Streptomyces* sp. can also be utilized.

Herein, the "protease from *Bacillus* sp." or the "protease from a microorganism *Bacillus*" may be the protease itself generated by the microorganism belonging to *Bacillus* sp., and widely includes variants obtained by substitutions, additions, deletions or insertions of one or more amino acids within the amino acid sequence of the protease and capable of increasing a concentration of fructosyl valylhistidine as the wild type protease from *Bacillus* sp.

Likewise, the "protease from *Aspergillus* sp." or the "protease from a microorganism *Aspergillus*" may be the protease itself generated by the microorganism belonging to *Aspergillus* sp., and widely includes variants obtained by substitutions, additions, deletions or insertions of one or more amino acids within the amino acid sequence of the protease and capable of increasing the concentration of fructosyl valine as the wild type protease from *Aspergillus* sp.

Even in the proteases from other origins, the wild type protease and the variants thereof capable of increasing the concentration of fructosyl valylhistidine or fructosyl valine are widely included.

The method for allowing the protease to act upon glycohemoglobin includes that first the sample containing glycohemoglobin is mixed and reacted with buffer containing a surfactant, and then the resulting solution is contacted with a protease solution or a protease immobilized onto support for a certain time, and any methods may be used.

Reaction conditions such as a protease concentration, a reaction pH and a reaction temperature are appropriately selected depending on the used protease. As one example, Protin PC10F (from Daiwa Kasei K.K.) is used in solution, as the reaction conditions of the sample containing glycohemoglobin with the buffer containing the surfactant, 0.1 to 50 mg/mL of the concentration of Protin PC10F, 20 to 50° C. of the reaction temperature and 6.0 to 9.0 of the reaction pH during the proteolysis can be exemplified when the concentration of the blood cells is 5 to 20% by volume.

Furthermore, it has been found that protease can digest hemoglobin efficiently in a short time by the protease immobilized onto an insoluble support at high density. The amount of protease immobilized onto the insoluble support is 1 to 50 mg/column, preferably 1 to 20 mg/column, more preferably 1 to 10 mg/column and particularly preferably 5 to 10 mg/column.

It is desirable that the surfactant for the digestion of the sample containing glycohemoglobin has two functions to hemolyze blood cell and to change a molecular structure of hemoglobin. Most of hemoglobin is present within erythrocytes, and in the presence of the surfactant at an appropriate concentration, hemoglobin is released out of the erythrocytes. Hemoglobin is usually folded, but is unfolded in the surfactant at the appropriate concentration. Thus, it is supposed that these function makes the digestion by the protease easy. As the surfactant, nonionic polyoxyethylene alkyl ethers [e.g., polyoxyethylene(10)octylphenyl ether (Triton X-100), polyoxyethylene(23)lauryl ether], polyoxyethylene sorbitan fatty acid esters [e.g., polyoxyethylene sorbitan monolaurate (Tween 20), polyoxyethylene sorbitan monopalmitate (Tween 40)], anionic polyoxyethylene alkyl ethers, alkyl sulfates [sodium dodecyl sulfate (SDS)], cationic ones, amphoteric ones such as alkyl betaines are available. The anionic surfactants are desirable because the two functions described above are large. Its concentration is 0.05 to 10% and preferably 0.05 to 1%, and a reaction time with the surfactant is about several seconds to about 10 minutes.

The buffer for the digestion of the sample containing glycohemoglobin is not particularly limited except for its pH range at which hemoglobin can be dissolved. Any well-known buffer, such as a phosphate buffer and a Tris buffer could be used. A salt such as sodium chloride and potassium chloride may be added appropriately in the buffer.

Fructosyl peptide oxidase which acts upon the fructosyl peptide includes, for example, fructosyl peptide oxidase described in JP 2001-95598-A, JP 2003-235585-A and JP 2004-275013-A.

In addition to these enzymes, the enzyme which specifically acts upon the fructosyl dipeptide and catalyzes the reaction to produce hydrogen peroxide can be obtained from nature by searching enzymes originating from microorganisms, animals or plants. Such an enzyme can be obtained by modifying known fructosyl amino acid oxidase from *Corynebacterium* sp., *Aspergillus* sp., *Fusarium* sp., *Gibberella* sp., *Penicillium* sp., and *Bacillus* sp.

In one preferable embodiment of the present invention, for the measurement of glycohemoglobin, it is preferable that fructosyl peptide oxidase does not substantially act upon fructosyl valylleucine which is the fructosyl peptide at the N terminus of the α-chain in the glycohemoglobin, fructosyl valine which is the fructosyl amino acid and fructosyl lysine glycated at ε-amino group, and specifically acts upon fructosyl valylhistidine which is the fructosyl peptide at the N terminus of the β-chain in the glycohemoglobin. It is because HbA1c is defined as hemoglobin glycated at the N terminus of the β-chain, and because it is likely that fructosyl valylleucine or fructosyl valine from the N terminus of α-chain in the glycohemoglobin and ε-fructosyl lysine liberated from glycated albumin in serum and fructosyl lysine contained in hemoglobin give positive errors to the measurement result.

However, as described in JP 2004-275013, many fructosyl peptide oxidases react with not only fructosyl peptide but also fructosyl valine. In such a case, produced fructosyl valine gives interferences occurring positive errors, and therefore, accuracy is not high. The method for preventing the interferences of fructosyl valine includes the method in which fructosyl valine in the glycohemoglobin solution treated with the protease is specifically detected and a subtractive operation is performed, and the method in which the treatment with the protease is performed under the condition where fructosyl valine is not produced. The latter method is desirable for obtaining high accuracy. In the latter case, it is important not to detect fructosyl valine in the solution treated with protease. Specifically, a detection system of fructosyl valine could be placed downstream of the sample injection machinery, confirming that detected amounts do not increase/decrease. At that time, a requirement for the used detection system of fructosyl valine is not to react with fructosyl peptides and to specifically detect fructosyl valine. It is particularly preferable to place the immobilized enzyme of fructosyl amino acid oxidase with such a property downstream of the sample injection machinery to detect the increase/decrease of hydrogen peroxide.

Additionally, fructosyl peptide oxidase can react with ε-fructosyl lysine and various amino acids. When fructosyl peptide oxidase reacts with these components, as fructosyl valine described above, it is desirable that these are not detected in the solution of protease treatment. In the case of ε-fructosyl lysine, as with the above, oxidase, which specifically acts upon ε-fructosyl lysine, may be used, and it may be replaced with that lysine which is non-glycated one of ε-fructosyl lysine is not detected in the solution of protease treatment. The latter is more desirable because it is simpler. To detect the amino acid, the method of placing the immobilized enzyme in which amino acid oxidase acting upon the substrate amino acid has been immobilized downstream of the sample injection machinery to detect the increase/decrease of hydrogen peroxide is particularly preferable in terms of easy operation and the simple apparatus constitution. As examples, it is desirable in terms of the thermostability and the sensitivity to use L-glutamate oxidase and L-lysine oxidase.

A digestion time of the protease can be defined by measuring fructosyl valine and the particular amino acid simultaneously with fructosyl valylhistidine in the sample solution containing the glycated protein treated with the protease. That is, the protease could digest within the time that fructosyl valine and the particular amino acid are not detected and only fructosyl valylhistidine is detected.

The origins of fructosyl amino acid oxidase include microorganisms belonging to *Corynebacterium* sp., *Aspergillus* sp., *Fusarium* sp., *Gibberella* sp., *Penicillium* sp. and *Bacillus* sp.

As the immobilization procedures of the enzyme in the present invention, well-known immobilization procedures of the protein such as a physical absorption method, an ionic bond method, an entrapment method and a covalent bond method can be utilized. Among them, the covalent bond method is desirable because it has excellent long-term stability. As the means for covalently binding the protein, the compound with aldehyde group such as formaldehyde, glyoxal and glutaraldehyde, a multifunctional acylating agent, cross-linking with a sulfhydryl group, and the like can be utilized. As the form of the immobilized enzyme, the enzyme can be immobilized on a film, which can be then placed on an electrode composed of platinum, gold or carbon, or the enzyme can be immobilized onto an insoluble support, which can be then packed with a column reactor.

Furthermore, it also improves the property such as film strength and substrate permeability of the immobilized enzyme by coimmobilizing the other enzyme, the protein such as gelatin and serum, and a synthetic polymer such as polyallylamine and polylysine. As the insoluble support for the enzyme immobilization, well-known supports such as diatom earth, active carbon, alumina, titanium oxide, cross-linked starch particles, cellulosic polymers, chitin derivatives and chitosan derivatives can be utilized.

Glucose, the fructosyl peptide and the fructosyl amino acid produced from glycohemoglobin in the sample by proteases are sequentially converted into hydrogen peroxide by glucose oxidase, fructosyl peptide oxidase and fructosyl amino acid oxidase (in random order). The concentration of each substance can be determined by the electrochemical detection of hydrogen peroxide produced by each oxidase. However, a ratio of glycohemoglobin in vivo is usually about 5%, which is low. Thus, it is sufficiently predicted that the amount of hydrogen peroxide from fructosyl valylhistidine or fructosyl valine by the proteolysis is little. Therefore, it is necessary to detect hydrogen peroxide with high sensitivity. Hemoglobin itself has an absorbance zone around 400 to 600 nm. Thus, because hemoglobin largely interfere with the detection of hydrogen peroxide absorbance in this wavelength region, the well-known methods can not be applied to the actual measurement of glycohemoglobin. From these reasons, it is more preferable to use an electrochemical detection technique such as amperometry for the high sensitive determination of hydrogen peroxide.

In one preferable embodiment of the present invention, the glucose and glycohemoglobin in the sample can be measured in one apparatus.

In the measurement of glucose in the present invention, the enzyme which catalyzes the oxidation of glucose is immobilized to use. As the corresponding enzymes, glucose oxidase (EC 1.1.3.4), pyranose oxidase (EC1.1.3.10) and glucose dehydrogenase (EC 1.1.99.10) are available. Among them, glucose oxidase is desirable because it is excellent in operational stability and substrate specificity.

Glucose concentration in clinical laboratories is ordinarily evaluated as glucose in plasma. The glucose concentration in whole blood is different from the glucose concentration in plasma because components such as hemoglobin which can not become the solvent are included in the whole blood. The measurement of the ratio of glycohemoglobin is intended the sample containing hemoglobin, that is, the whole blood or blood cells. When the ratio of glycohemoglobin and glucose are simultaneously measured in whole blood sample, the detected glucose concentration is the glucose concentration in the whole blood.

The glucose concentration in the whole blood is nearly equivalent to the glucose concentration in the blood cells (erythrocytes) in fresh blood. Thus herein, the glucose concentration in the whole blood and the glucose concentration in the blood cells (erythrocytes) are not distinguished to represent as the "glucose concentration in the whole blood" in some cases.

As the method for calculating the glucose concentration in the plasma from the glucose concentration in the whole blood, the method in which a hematocrit value is measured by some methods to correct the glucose concentration in the whole blood (hematocrit correction) is available. However, because this method requires another apparatus for measuring the hematocrit value, the apparatus is large-scale and complicated, and thus is not desirable. In the embodiments of the present invention, when the ratio of glycohemoglobin is measured, the hemoglobin concentration is surely measured. Thus, the glucose concentration in the plasma can be calculated without the large-scale apparatus by comprising the second arithmetic system in which a correction factor for glucose in blood cells is calculated from the hemoglobin concentration to correct the glucose concentration in the whole blood.

However, the present inventors have found that fructosyl amino acid oxidase acts upon not only the fructosyl amino acid, but also glucose. In the blood, the concentration of glucose is about 100 times greater than that of glycohemoglobin. Thus, when fructosyl amino acid oxidase acts upon glucose, the detected amount of fructosyl valine includes the positive error due to glucose, and the exact concentration of fructosyl valine is not obtained. Therefore, in order to eliminate the interference of the detected amount of fructosyl valine from glucose in the sample, an immobilized glucose oxidase is placed together with an immobilized fructosyl amino acid oxidase, the fructosyl valine is measured simultaneously with glucose, and the subtractive operation is performed between the detected fructosyl valine and the interference from glucose in the sample using the third arithmetic system.

In the measurement of the fructosyl peptide, fructosyl peptide oxidase which oxidizes the fructosyl peptide to produce hydrogen peroxide is immobilized to use. Upon detection of fructosyl valylhistidine which is the fructosyl dipeptide at the N terminus of glycohemoglobin, the requirement for fructosyl peptide oxidase is preferably not to substantially act upon fructosyl valylleucine which is the fructosyl dipeptide at N terminus of the α chain and ε-fructosyl lysine glycated at ε-amino group and to specifically act upon fructosyl valylhistidine which is the fructosyl dipeptide at the N terminus of β-chain in the glycohemoglobin.

As is the case with fructosyl amino acid oxidase, when fructosyl peptide oxidase also acts upon glucose, the immobilized glucose oxidase is used simultaneously, the fructosyl peptide and glucose are simultaneously measured, and the subtractive operation is performed between the detected fructosyl peptide and the interference from glucose in the sample using the third arithmetic system.

In a detection system of the fructosyl amino acid or the fructosyl peptide using fructosyl amino acid oxidase or fructosyl peptide oxidase, when glucose in the sample interferes the detection of the fructosyl amino acid or the fructosyl peptide, an arithmetic system for eliminating this interference is described. Specifically, when the fructosyl amino acid or the fructosyl peptide responds in the glucose detection system and glucose responds in the detection system of the fructosyl amino acid or the fructosyl peptide, first, glucose and fructosyl amino acid or fructosyl peptide is calibrated in each detection system. Subsequently, a resulting response value for the sample in each detection system is obtained by the subtractive operation using each calibration curve.

The calibration curve for glucose obtained in the glucose detection system combining the immobilized glucose oxidase with an electrode for hydrogen peroxide is $$Y=a_{11} \times X + b_{11};$$

the calibration curve for fructosyl valine or fructosyl valylhistidine is $$Y=a_{12} \times X + b_{12};$$

the calibration curve for the glucose obtained in the detection system of the fructosyl amino acid or the fructosyl peptide combining the immobilized fructosyl amino acid oxidase or fructosyl peptide oxidase with the electrode for hydrogen peroxide is $$Y=a_{21} \times X + b_{21};$$

and the calibration curve for fructosyl valine or fructosyl valylhistidine is $$Y=a_{22} \times X + b_{22},$$

the responses to glucose at concentration of $X_1$ and fructosyl valine at concentration of $X_2$ are $$Y_1=a_{11} \times X_1 + b_{11} + a_{12} \times X_2 + b_{12}$$

in the first electrode for hydrogen peroxide, and $$Y_2=a_{21} \times X_1 + b_{21} + a_{22} \times X_2 + b_{22}$$

in the second electrode for hydrogen peroxide.

Based on these values, when the concentrations of glucose, fructosyl valine or fructosyl valylhistidine are calculated, the concentration $X_1$ of glucose is $$X_1=[a_{12} \times (Y_2-b_{21}-b_{22}) - a_{22} \times (Y_1-b_{11}-b_{12})]/(a_{12} \times a_{21} - a_{11} \times a_{22}),$$

and the concentration $X_2$ of fructosyl valine or fructosyl valylhistidine is $$X_2=[a_{11} \times (Y_2-b_{21}-b_{22}) - a_{21} \times (Y_1-b_{11}-b_{12})]/(a_{11} \times a_{22} - a_{12} \times a_{21}).$$

Even when fructosyl valine or fructosyl valylhistidine responds in the glucose detection system and glucose responds in the immobilized fructosyl amino acid oxidase or the immobilized fructosyl peptide oxidase, it is possible to calculate the concentrations of glucose and fructosyl valine or fructosyl valylhistidine, and quantify them separately.

When fructosyl valine or fructosyl valylhistidine does not respond in the glucose detection system, $a_{12}$ and $b_{12}$ in the above formula are 0, and the concentration $X_1$ of glucose is $X_1=(Y_1-b_{11})/a_{11}$ and the concentration $X_2$ of fructosyl valine or fructosyl valylhistidine is $X_2=[a_{11} \times (Y_2-b_{21}-b_{22}) - a_{21} \times (Y_1-b_{11})]/(a_{11} \times a_{22})$. Thus, glucose and fructosyl valine or fructosyl valylhistidine are calibrated in the glucose detection system and the detection system of the fructosyl amino acid or the fructosyl peptide, and the glucose concentration and the concentration of fructosyl valine or fructosyl valylhistidine in the sample can be precisely calculated by the above formula from the detected fructosyl valine or fructosyl valylhistidine.

Furthermore, the HbA1c value, which is the ratio of glycohemoglobin, is obtained by calculating the ratio of the fructosyl valine or fructosyl valylhistidine concentration eliminating the interference from glucose in the sample to the hemoglobin concentration in the sample using the first arithmetic system.

In the method of treating glycohemoglobin with the protease, first the sample containing glycohemoglobin is mixed with the buffer containing the surfactant. Next, the protease is added and reacted for the given time, or alternatively the sample containing glycohemoglobin has been mixed with the buffer containing the surfactant, and then is contacted with the support onto which the protease has been immobilized for the given time. Any of these methods may be used.

To allow the reaction to progress by contacting the sample with the immobilized enzyme, a batch type in which a sample solution is reacted with stirring for the certain time can be utilized. However, to perform the measurement with higher accuracy, it is desirable to use a flow type. In the present invention, the apparatus employing the flow type which can perform the measurement with higher accuracy is disclosed.

HbA1c, which is intended to the measurement of the ratio of glycohemoglobin as a clinical diagnostic indicator, is represented by the ratio of a fraction glycated at a particular site to total hemoglobin. Thus, when the hemoglobin concentration in the sample is determined, the ratio of a fructosyl valylhistidine amount or a fructosyl valine amount detected in the sample to total hemoglobin could correspond.

As the determination method of the hemoglobin concentration, well-known methods such as the cyanmethemoglobin method, methemoglobin method, azide hemoglobin method and SLS-hemoglobin method may be used. Among them, the SLS-hemoglobin method is preferable because influences of various enzymes such as inhibition and inactivation are scarcely given and little problem of environmental pollution is raised upon disposal of reagents. In the SLS-hemoglobin method, a blood sample is treated with an alkyl sulfate salt solution (hereinafter represented as a hemoglobin determination reagent) which is the anionic surfactant, and subsequently the hemoglobin concentration is calculated from the change of the absorbance at 540 nm. As the alkyl sulfate salt, sodium lauryl sulfate (SLS), sodium polyoxyethylene lauryl sulfate may be appropriately selected to use, and the buffer and various salts may be contained in the hemoglobin determination reagent. The concentration of the alkyl sulfate salt is 0.05 to 10% and preferably 0.05 to 1% relative to 0.25 to 20% by volume of a blood cell concentration in the reaction solution. The reaction of the blood sample with the hemoglobin determination reagent is completed within several seconds to several minutes.

The buffer containing the surfactant for the proteolysis can be contained in the hemoglobin determination reagent containing the alkyl sulfate salt, and then the hemolysis, the denaturation of hemoglobin and the formation of SLS-hemoglobin may be performed simultaneously, or alternatively the buffer containing the surfactant for the proteolysis may be added after the sample is reacted with the hemoglobin determination reagent, or alternatively these may be performed in converse order.

The surfactant in the hemoglobin determination reagent and the surfactant for the proteolysis may be different or the same as long as they satisfy the above conditions.

The hemoglobin concentration may be measured within the time when the absorbance of the reaction solution is stable after the reaction of the sample with the hemoglobin determination reagent, and may be measured before or after the proteolysis of the sample or before or after the detection of glucose and fructosyl valylhistidine and fructosyl valine.

As the means of measuring the absorbance in the solution treated with the hemoglobin determination reagent, a batch method in which the sample is dispensed in a cuvette and the sample absorbance at a particular wavelength is measured, or a flow method in which Teflon (registered trademark) tube is used as a cell and the absorbance change at the particular wavelength is measured when the sample passes through the Teflon (registered trademark) tube could be usable. The flow method is more desirable because of its simple operation. The hemoglobin concentration may be measured within the time when the absorbance in the reaction solution is stable after the treatment of the sample with the hemoglobin determination reagent.

One preferable embodiment of the present invention using the protease for the treatment of the sample which produces fructosyl valylhistidine is shown in FIG. 1. Buffer pumping machineries (1, 2) and sample injection machineries (4, 5, 7) are comprised. A protease-immobilized enzyme (14), a flow type calorimeter for detecting the hemoglobin concentration (16) and electrodes (18, 20) which can detect the concentration of electroactive components are placed downstream sample injection machineries (4, 5, 7). It is constituted by an electrode system (17, 18) for the detection of the fructosyl peptide, an electrode system (19, 20) for the detection of the amino acid or the fructosyl amino acid. Furthermore, (3) and (15) represent a damper and a mixing coil, respectively.

Specifically, the buffer is pumped out from a buffer tank (1) using a pump (2). A needle (7) is inserted into the sample (6), and then a valve (10) is closed, a valve (11) is opened, and by going a syringe pump (12) the sample is transferred to a sample loop (5) in the injection valve (4). Subsequently, the injection valve (4) is switched and the sample in the sample loop (5) is pushed out. The excessive sample is pushed out to a waste pot (8) and collected in a waste tank (23) by once opening the valve (10) and closing the valve (11) to go in a washing solution in the syringe pump (12), subsequently closing the valve (10) and opening the valve (11) to push out the washing solution. The injected sample transfers with the flowing buffer and passes through a protease-immobilized column (14) placed in an incubator (13), which produces the fructosyl peptide from the glycated protein in the sample. The sample treated with the protease transfers with the flowing buffer and passes through the flow type calorimeter (16) further downstream. After the hemoglobin concentration in the sample is detected, the sample passes through a fructosyl peptide oxidase-immobilized column (17), and the produced hydrogen peroxide is detected by the electrode for hydrogen peroxide (18). Subsequently, the sample passes through an amino acid oxidase-immobilized column or a fructosyl amino acid oxidase-immobilized column (19), and the produced hydrogen peroxide is detected by an electrode for hydrogen peroxide (20) downstream. A waste solution passes through a back pressure coil (21) to collect in the waste tank (22). The blood sample (6) can be injected in the apparatus, or be injected after the previous treatment with a hemoglobin determination reagent and/or the treatment with the protease. In the former, a hemoglobin determination reagent is injected together with the protease, and then the sample is reacted with the hemoglobin determination reagent and the protease in a flow path of the buffer. The substance concentrations are quantified by detecting the absorbance change in the flow type calorimeter (16) and the changes of current amounts in the electrodes (18) and (19) for hydrogen peroxide.

An apparatus for assaying glycohemoglobin in another embodiment can be constituted by using an electrode system (17, 18) for fructosyl amino acid and an electrode system (19, 20) for the amino acid in place of the electrode system (17, 18) for fructosyl peptide and the electrode system (19, 20) for the amino acid or fructosyl amino acid in the apparatus in FIG. 1, and producing fructosyl valine from the glycated protein in the sample by the protease-immobilized column (14).

The apparatus in FIG. 1 can also be used as one preferable embodiment of the present invention, which simultaneously determines glucose and glycohemoglobin. That is, when the electrode system (17, 18) for detecting glucose and the electrode system (19, 20) for detecting the fructosyl amino acid or the fructosyl peptide are used in place of the electrode system (17, 18) for detecting fructosyl peptide, the electrode system (19, 20) for detecting the amino acid or fructosyl amino acid in the apparatus in FIG. 1, the glucose and glycohemoglobin can be simultaneously determined.

Specifically, the sample passes through a glucose oxidase-immobilized enzyme (17), and the produced hydrogen peroxide is detected in the electrode (18) for hydrogen peroxide. Subsequently, the sample passes through the fructosyl amino acid oxidase-immobilized enzyme or the fructosyl peptide oxidase-immobilized enzyme (19), and the produced hydrogen peroxide is detected in the downstream electrode (20) for hydrogen peroxide. The waste solution passes through the back pressure coil (21) to collect in the waste tank (22).

Figure 2:
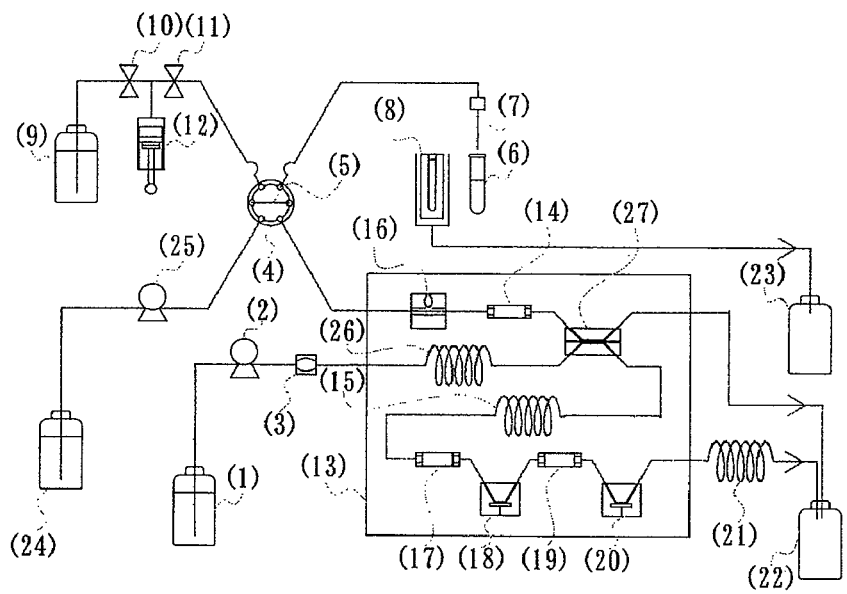
FIG. 2 shows a schematic assay apparatus.

FIG. 2 is an example of a flow type apparatus for a simultaneous measurement of glucose and the fructosyl amino acid or the fructosyl peptide, in which a dialysis module is capable of continuously eliminating contaminations of a measurement system due to the blood sample. The buffer B is pumped out from a buffer tank (24) using a pump (25). The sample (6) is injected into the flowing buffer B by sample injection machineries (4, 5, 7). The injected sample transfers with the flowing buffer B, and passes through a flow type calorimeter (16) placed in the incubator (13). The hemoglobin concentration is detected from the absorbance change at the certain wavelength. Subsequently, the sample passes through a protease-immobilized column (14) further downstream, and the fructosyl amino acid or the fructosyl peptide is produced from the glycated protein in the sample. The sample treated with the protease is carried to the dialysis module (27) further downstream, and only components with low molecular weight in the sample are led through a regenerated cellulose membrane with a membrane thickness of 20 μm and molecular weight cut off of 12,000 to 14,000 to systems (17, 18, 19, 20) to detect glucose and the fructosyl amino acid or the fructosyl peptide. Since the buffer A is pumped out from the buffer tank (1) using the pump (2), components with low molecular weight in the sample dialyzed in the dialysis module (27) pass through the glucose oxidase-immobilized enzyme (17) and the electrode (18) for hydrogen peroxide, and hydrogen peroxide produced in the glucose oxidase-immobilized enzyme (17) is detected. Subsequently, components with low molecular weight pass through the fructosyl amino acid oxidase-immobilized column or the fructosyl peptide oxidase-immobilized column (19) and the electrode (20) for hydrogen peroxide, and produced hydrogen peroxide is detected. Components with high molecular weight in the sample which do not pass through the dialysis membrane in the dialysis module (27) are collected in the waste tank (22), and (26) represents the coil for thermostabilization.

For the membrane (27) used in the separation system of the components with low molecular weight in the sample after the proteolysis, it is required that pentapeptide and hexapeptide and larger peptides to coexist in the proteolysis process are hardly permeated or not permeated at all, and fructosyl valine and fructosyl valylhistidine are permeated. As the usable membrane, the dialysis membranes made from regenerated cellulose, acetylcellulose and polyvinylidene fluoride can be exemplified. A molecular weight cut off of the dialysis membrane is represented by a permeated minimum molecular weight on an equilibrium dialysis. Meanwhile, for the purpose of the analysis, the separation is often performed by the difference of initial rates in the dialysis, and the fractionated molecular weight does not always agreed with the molecular weight cut off. For the purpose of the present invention, the dialysis membrane with the molecular weight cut off is 300 to 500,000, more preferably 1,000 to 100,000 and more desirably 10,000 to 20,000.

The blood sample (6) is injected into the apparatus after treating it with the hemoglobin determination reagent, or is injected into the apparatus after treating it with the hemoglobin determination reagent and further protease. In the injection of the blood sample further treated with the protease, for example, the sample treated with the hemoglobin determination reagent can be injected together with the protease, and be treated with the protease in the flow path of the buffer. The hemoglobin concentration can be determined from the absorbance change at the certain wavelength in the flow type calorimeter (16), and the concentrations of glucose and the fructosyl amino acid or the fructosyl peptide can be quantified from detecting the current change in the electrodes (18) and (20) for hydrogen peroxide.

The buffer flowing in these apparatuses is not particularly limited, and the pH can be selected (e.g., pH 7 to 9) so that the immobilized enzymes (14, 17, 19) are activated. Antibacterial agents and surfactants may be added at concentrations which do not interfere with the immobilized enzymes (14, 17, 19) and the electrodes (18, 20) for hydrogen peroxide. Activators of the immobilized enzymes (14, 17, 19) which do not interfere with the electrodes (18, 20) for hydrogen peroxide may be included.

In the apparatus shown in FIG. 2, it is possible to use the combination of the fructosyl peptide oxidase-immobilized column (17) and the amino acid oxidase-immobilized column, or the fructosyl amino acid oxidase-immobilized column (19), or the combination of the fructosyl amino acid oxidase-immobilized column (17) and the amino acid oxidase-immobilized column (19), in place of the glucose oxidase-immobilized enzyme (17) and the fructosyl amino acid oxidase-immobilized column, or the fructosyl peptide oxidase-immobilized column (19).

EXAMPLES

The present invention will be described more specifically by the following Examples. These examples are not intended to limit of the technical scope of the present invention.

Example 1

(1) Production of Fructosyl Peptide Oxidase-Immobilized Column

Firebrick powder (150 mg, 30 to 60 meshes) was thoroughly dried, immersed in a 10% solution of γ-aminopropyltriethoxysilane in anhydrous toluene for one hour, then thoroughly washed with anhydrous toluene and dried. The aminosilane-modified support was immersed in a 5% aqueous glutaraldehyde solution for one hour, and then thoroughly washed with distilled water, followed by substitution with 100 mM sodium phosphate buffer (pH 7.0). The buffer was removed as far as possible. A solution (200 mL) of fructosyl peptide oxidase (140 units/mL, from Kikkoman Co.) in 100 mM sodium phosphate buffer (pH 7.0) was contacted with the formylated firebrick powder, and then incubated at 0 to 4° C. for one day for the enzyme immobilization. The support immobilized enzyme was packed into a column (internal diameter: 3.5 mm, length: 30 mm) to give the fructosyl peptide oxidase-immobilized column.

(2) Production of Electrode for Hydrogen Peroxide

A side face of a platinum wire with a diameter of 2 mm was covered with heat-shrinking Teflon (registered trademark), and one end of the wire was smoothed using a file and emery paper No. 1500. This platinum wire was used as a working electrode, a platinum plate with 1 cm square was used as a counter electrode, and a saturated calomel electrode was used as a reference electrode; an electrolytic treatment was performed in 0.1 M sulfuric acid at +2.0 V for 10 minutes. Subsequently, the platinum wire was thoroughly washed with water, dried at 40° C. for 10 minutes, then immersed in a 10% solution of γ-aminopropyltriethoxysilane in anhydrous toluene for one hour and washed. Glutaraldehyde was added to a solution of bovine serum albumin (20 mg) (fraction V, from Sigma-Aldrich Co.) in 1 mL of distilled water to a glutaraldehyde concentration of 0.2%. This mixed solution (5 μL) was expeditiously placed on the platinum wire prepared as described above, and dried and cured at 40° C. for 15 minutes. This was used as the electrode for hydrogen peroxide.

A Ag/AgCl reference electrode was used as the reference electrode, and a conductive piping was used as the counter electrode.

(3) Assay Apparatus

Assay apparatus for fructosyl peptide was shown in FIG. 1. The buffer was pumped out from a buffer tank (1) using a pump (2), and 5 μL of a sample was injected using a valve (4). A protease-immobilized column (14), a flow type calorimeter (16), a second immobilized enzyme column (19) and a second electrode for hydrogen peroxide (20) were not placed, and a fructosyl peptide oxidase-immobilized column was placed as a first immobilized enzyme column (17), followed by an electrode for hydrogen peroxide (18) downstream thereof. The injected sample transferred with the flowing buffer, passed through a mixing coil (15) inside an incubator (13), and thus the sample temperature was adjusted and the sample was mixed with the buffer. The sample passed through the fructosyl peptide oxidase-immobilized column (17) and the electrode for hydrogen peroxide (18) to produce hydrogen peroxide from fructosyl valylhistidine in the sample, and then the change of the current was detected.

A composition of the buffer used in this assay apparatus contained 100 mM phosphoric acid, 50 mM potassium chloride and 1 mM sodium azide, and its pH was 7.0.

The flow rate of the buffer was 1.0 mL/minute, and the temperature in the incubator was 30° C.

(4) Characteristics of Fructosyl Peptide Oxidase-Immobilized Column

Using the assay apparatus described in (3), a 5 μL portion of fructosyl glycine, fructosyl valine or fructosyl valylhistidine was injected, and the characteristics of the fructosyl peptide oxidase-immobilized column was examined. Results were shown below.

(i) pH Profile

Figure 3:
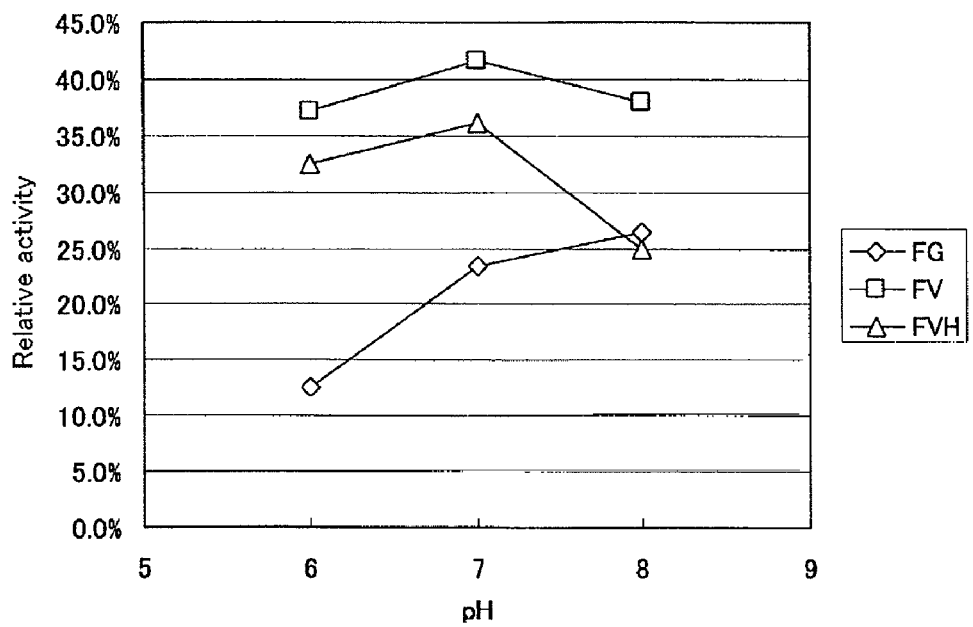
FIG. 3 is a graph showing pH profile of immobilized enzymes.

When pH of the buffer was 6.0, 7.0 or 8.0, the assay results of the activity for the oxidation of fructosyl glycine (FG), fructosyl valine (FV) or fructosyl valylhistidine (FVH) were shown in FIG. 3. For fructosyl glycine the activity was high at pH 8.0, but the activity at pH 6.0 was decreased to about 50% of that at pH 8.0. For fructosyl valine and fructosyl valylhistidine, the activity was high at pH 6.0 and 7.0.

Since the activity for fructosyl glycine was low in acidic pH, it was suggested that the activities for other fructosyl amino acids were lowered. Since the activities for fructosyl valylhistidine and fructosyl valine were maximized at pH 7.0, pH 7.0 was selected as optimum in the determination of fructosyl valylhistidine.

(ii) Substrate Specificity

The substrate specificity on the fructosyl peptide oxidase-immobilized column was shown in Table 1. Response values in Table 1 were normalized to 100 for the response to fructosyl valine at each pH.

At any pH, the immobilized enzyme column was specific for fructosyl valylhistidine and fructosyl valine, scarcely responded to α, ε-fructosyl lysine, and did not respond at all to other amino acids and sugars.

TABLE 1

| No. | Sample name | Relative activity (%) | | |
|---|---|---|---|---|
| | | pH 6.0 | pH 7.0 | pH 8.0 |
| 1 | Fructosyl glycine | 35 | 56 | 70 |
| 2 | Fructosyl valine | 100 | 100 | 100 |
| 3 | α, ε-Fructosyl lysine | 9 | 10 | 11 |
| 4 | Fructosyl valyl histidine | 88 | 87 | 66 |
| 5 | Lys | 0 | 0 | 0 |
| 6 | Glu | 0 | 0 | 0 |
| 7 | Gln | 0 | 0 | 0 |
| 8 | Ala | 0 | 0 | 0 |
| 9 | Asp | 0 | 0 | 0 |
| 10 | Phe | 0 | 0 | 0 |
| 11 | Gly | 0 | 0 | 0 |
| 12 | His | 0 | 0 | 0 |
| 13 | Leu | 0 | 0 | 0 |
| 14 | Arg | 0 | 0 | 0 |
| 15 | Ser | 0 | 0 | 0 |
| 16 | Thr | 0 | 0 | 0 |
| 17 | Val | 0 | 0 | 0 |
| 18 | Trp | 0 | 0 | 0 |
| 19 | Met | 0 | 0 | 0 |
| 20 | Asn | 0 | 0 | 0 |
| 21 | Pro | 0 | 0 | 0 |
| 22 | Mannose | 0 | 0 | 0 |
| 23 | Glucose | 0 | 0 | 0 |
| 24 | Fructose | 0 | 0 | 0 |
| 25 | D-Sorbitol | 0 | 0 | 0 |
| 26 | Glycerol | 0 | 0 | 0 |
| 27 | Galactose | 0 | 0 | 0 |
| 28 | Xylose | 0 | 0 | 0 |

(iii) Stability

Under the condition of the buffer at pH 7.0, the flow rate of the buffer at 1.0 mL/minute and the incubator temperature at 30° C., the activity for fructosyl valine was decreased to about 50% of its original activity in the fructosyl peptide oxidase-immobilized column after 10 days. The used fructosyl peptide oxidase-immobilized column did not substantially act upon α, ε-fructosyl lysine, and specifically acted upon fructosyl valylhistidine and fructosyl valine. The optimal pH for fructosyl valine and fructosyl valylhistidine was neutral or acidic. Thus, it was desirable that the protease for the production of the fructosyl peptide from the glycated protein had high activity in the neutral or acidic region.

(5) Proteolysis of Blood Cells

Human hemoglobin was digested by the protease, and the fructosyl peptide oxidase-immobilized column with the optimal pH in the neutral or acidic region was used for the determination of produced fructosyl peptide. Therefore, the protease from *Bacillus* sp. was used because the activity to produce fructosyl valylhistidine was high in the neutral or acidic region.

Figure 4:
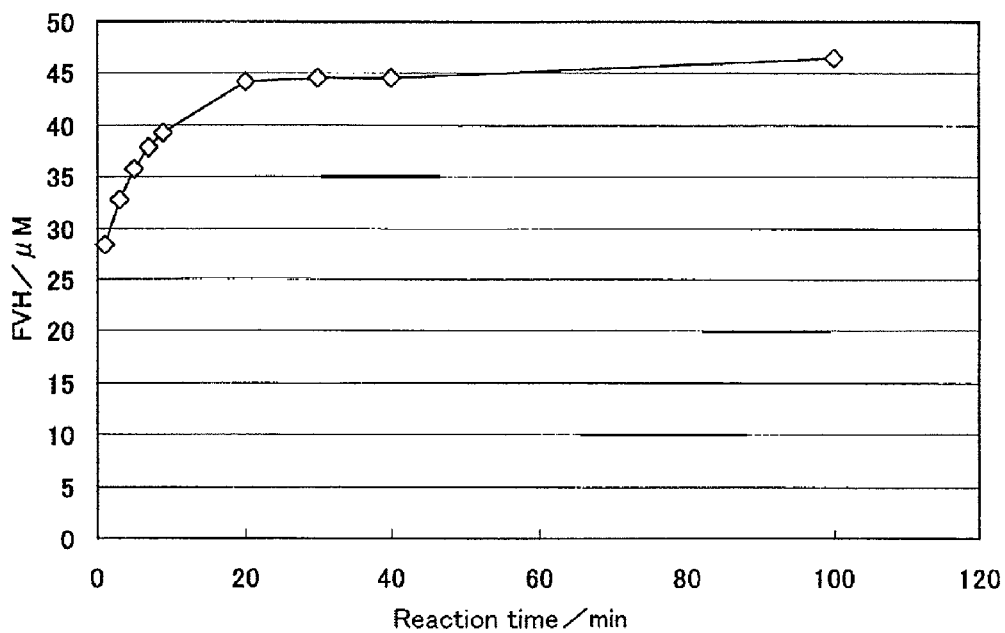
FIG. 4 is a graph showing a time course of proteolysis in a solution.

The blood cells were obtained by washing the human whole blood with saline and centrifuging at 2,000 g. The blood cells (200 μL) obtained were added to 750 μL of an aqueous solution of 0.5% sodium polyoxyethylene lauryl sulfate (pH 6.8), which was the anionic surfactant to hemolyze. Subsequently, 50 μL of 320 mg/mL Protin PC10F (from Daiwa Kasei K.K.), which was the protease from *Bacillus* sp., was added to the resulting solution, and was then reacted at 37° C. A 5 μL portion of this solution reacted with protease for 1, 3, 5, 7, 9, 20, 30, 40, or 100 minutes was injected into the assay apparatus described in (3), and fructosyl valylhistidine in the sample was determined. The results were shown in FIG. 4.

Under the same condition, fructosyl valylhistidine was not detected at all in the hemolyzate and in an enzyme blank solution in which blood cell was absent. Therefore, it was found that fructosyl valylhistidine was liberated within a short time by the action of used protease. This protease effectively liberated fructosyl valylhistidine from human hemoglobin.

(6) HbA1c Determination in Japanese Secondary Reference Material for HbA1c

Japanese secondary reference material for HbA1c (from Health Care Technology Foundation), with three different ratios of glycohemoglobin, was determined using the protease from *Bacillus* sp. and the present assay apparatus.

The Japanese secondary reference material for HbA1c was prepared according the procedure described in a product description. The prepared Japanese secondary reference material for HbA1c (60 μL) was hemolyzed in 225 μL of the aqueous solution of 0.5% sodium polyoxyethylene lauryl sulfate (pH 6.8), subsequently 15 μL of 320 mg/mL Protin PC10F (from Daiwa Kasei K.K.) was added, and then the mixture was reacted at 37° C. for 8.5 or 30 minutes. After the reaction, a 5 μL portion of the solution treated with the protease was injected into the assay apparatus described in (3), and the concentration of fructosyl valylhistidine in the sample was determined.

The concentration of hemoglobin in the solution treated with the protease was determined using hemoglobin B-Test Wako (from Wako Pure Chemical Industries, Ltd.) according to the procedure described in the product description.

Figure 5:
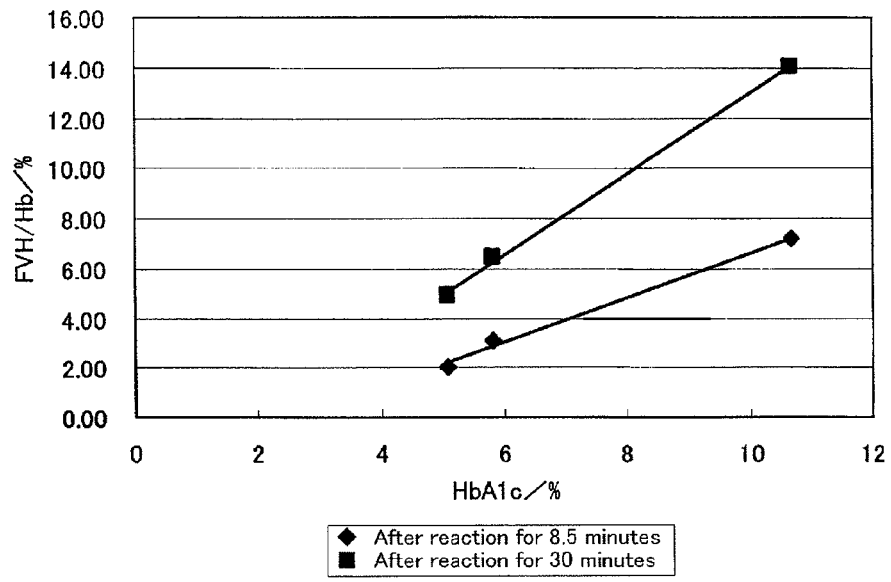
FIG. 5 is a graph showing correlation to Japanese secondary reference material for HbA1c.

The calculation results of the ratio (FVH/Hb) of the fructosyl valylhistidine concentration to the hemoglobin concentration determined in the Japanese secondary reference material for HbA1c at three levels (HbA1c values: 5.08±0.12%, 5.80±0.13% and 10.63±0.25%) were shown in FIG. 5.

Good linear relations with correlation coefficients of 0.9964 (Y=0.887x−0.155) and 0.9991 (Y=1.62x−1.17) for protease reaction time of 8.5 minutes and 30 minutes, respectively, were obtained.

Comparative Example 1

The proteolysis of hemolyzate was examined for proteases with different origins, optimal pH and manufacturers.

The used proteases were Umamizyme G, Protease A "Amano" G, Protease M "Amano" G, Protease N "Amano" G, Peptidase R and Neutrase F3G from Amano Enzyme Inc., and Flavorzyme, Neutrase and Protamex from Novozymes.

In the same method as Example 1(5), the hemolyzate was added at about 1 mg/mL in the reaction solution of the above protease, and the resulting solution was reacted at 37° C. for 40 minutes. After the reaction, a 5 μL portion of the solution treated with the protease was injected into the assay apparatus described in Example 1 (3). The results are shown in Table 2. In Table 2, result "A" represented which detected a value of 20 μM or more fructosyl valylhistidine, and result "B" represented those which did not detect value of 20 μM or more fructosyl valylhistidine.

TABLE 2

| | Product name | Origin | Manufacturer | Optimal pH | * |
|---|---|---|---|---|---|
| A | Umamizyme G | *Aspergillus oryzae* | Amano Enzyme | 8.0 | B |
| B | Protease "Amano" G | *Aspergillus oryzae* | Amano Enzyme | 7.0 | B |
| C | Protease M "Amano" G | *Aspergillus oryzae* | Amano Enzyme | 4.5 | B |
| D | Protease N "Amano" G | *Bacillus subtilis* | Amano Enzyme | 7.0 | A |
| E | Peptidase R | *Rhizopus oryzae* | Amano Enzyme | 7.0 | B |
| F | Neurase F3G | *Rhizopus niveus* | Amano Enzyme | 3.0 | B |
| G | Flavorzyme | *Aspergillus oryzae* | Novozymes | 7.0 | B |
| H | Neutrase | *Bacillus amyloliquefaciens* | Novozymes | 6.0 | A |
| I | Protamex | *Bacillus* sp. | Novozymes | 6.0 | A |

* Result

The hemoglobin concentration in whole blood is typically 120 to 160 g/L; in the present experiment, the solution is diluted 5 times, and thus the hemoglobin concentration in the reaction solution is 24 to 32 g/L. Furthermore, the normal human HbA1c value is about 5%, and thus the concentration of fructosyl valylhistidine in the reaction solution is estimated to be about 19 to 25 μM maximum. Therefore, if 2.0 μM or more fructosyl valylhistidine is detected, it is suggested that a digestion ratio is large.

Under the condition where the pH of the solution treated with the protease was around neutral, the proteases from *Bacillus* sp. exhibited the large detected value; however, in the other enzymes, 20 μM or more fructosyl valylhistidine was not detected. It was suggested that the protease from *Bacillus* sp. efficiently produced fructosyl valylhistidine from human blood cells at pH around neutrality.

Example 2

As shown in Example 1, the use of the protease from *Bacillus* sp. enabled the production of fructosyl valylhistidine from human blood cells. However, it was shown that fructosyl peptide oxidase used for the detection of fructosyl valylhistidine did not respond at all to various amino acids and sugars, but to fructosyl valine. To determine HbA1c with high accuracy, the proteolysis must be performed within the time that fructosyl valine and ε-fructosyl lysine i.e., L-lysine are not produced. For this purpose, in the case of using Protin PC10F (from Daiwa Kasei K.K.) as the protease, a time course of the treatment with the protease was examined in detail and the results were shown below.

(1) Production of Fructosyl Peptide Oxidase-Immobilized Column

The fructosyl peptide oxidase (from Kikkoman Co.)-immobilized column was produced in the same method as Example 1.

(2) Production of Fructosyl Amino Acid Oxidase-Immobilized Column

In the same method as Example 1, 150 mg of firebrick powder (30 to 60 meshes) was formylated. A solution (400 μL) of fructosyl amino acid oxidase (18 units/mL, from Kikkoman Co.) in 100 mM sodium phosphate buffer (pH 7.0) was contacted with the formylated firebrick powder, and then incubated at 0 to 4° C. for one day for the enzyme immobilization. The support immobilized enzyme was packed into a column (internal diameter: 3.5 mm, length: 30 mm) to give the fructosyl amino acid-oxidase immobilized column.

(3) Production of L-Lysine Oxidase-Immobilized Column

In the same method as Example 1, 150 mg of firebrick powder (30 to 60 meshes) was formylated. A solution (50 μL) of L-lysine oxidase (50 units/mL, from Kikkoman Co.) in 100 mM sodium phosphate buffer (pH 7.0) was contacted with the formylated firebrick powder, and then incubated at 0 to 4° C. for one day for the enzyme immobilization. The support immobilized enzyme was packed into the column (internal diameter: 3.5 mm, length: 30 mm) to give the L-lysine oxidase-immobilized column.

(4) Production of Electrode for Hydrogen Peroxide

The electrode for hydrogen peroxide was produced in the same method as Example 1.

(5) Assay Apparatus

As described in Example 1, the assay apparatus for fructosyl peptide shown in FIG. 1 was used. The buffer was pumped out from the buffer tank (1) using the pump (2), and a 5 μL portion of the sample was injected using the valve (4). The protease-immobilized column (14) and the flow type calorimeter (16) were not placed, and the fructosyl peptide oxidase-immobilized column was placed as the first immobilized enzyme column (17), the electrode for hydrogen peroxide (18) was placed, the L-lysine oxidase-immobilized column or the fructosyl amino acid oxidase-immobilized column as the second immobilized enzyme column (19) and the electrode for hydrogen peroxide (20) were placed downstream thereof. The injected sample transferred with the flowing buffer, passed through the mixing coil (15) inside the incubator (13), and thus the sample temperature was adjusted and the sample was mixed with the buffer. The sample passed through the fructosyl peptide oxidase-immobilized column (17) and the electrode for hydrogen peroxide (18), hydrogen peroxide was produced from fructosyl valylhistidine in the sample, and then the change of the current was detected. The sample further passed through the downstream L-lysine oxidase-immobilized column or fructosyl amino acid oxidase-immobilized column (19) and the electrode for hydrogen peroxide (20), L-lysine or fructosyl valine was converted to hydrogen peroxide, and the change of the current was detected.

The composition of the buffer used in this assay apparatus contained 100 mM phosphoric acid, 50 mM potassium chloride and 1 mM sodium azide, and its pH was 7.0.

The flow rate of the buffer was 1.0 mL/minute, and the temperature in the incubator was 30° C.

(6) Determination of Products in Blood Cell Solution Treated with Protease

Protin PC10F (from Daiwa Kasei K.K.) solution in 100 mM sodium phosphate buffer (pH 7.0) was added to the hemolyzate and reacted at 37° C. for the given time. A 5 μL portion of the resulting solution was injected in the assay apparatus described in (5), and the fructosyl valylhistidine concentration, the fructosyl valine concentration and the L-lysine concentration in the sample were determined simultaneously at each reaction time.

Figure 6:
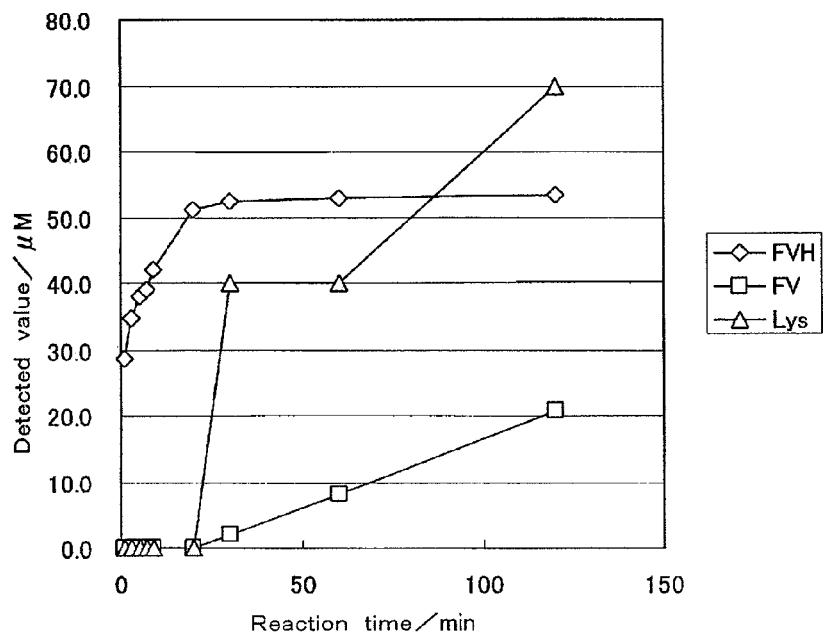
FIG. 6 is a graph showing a time course of proteolysis in hemolyzates of blood cell.

The blood cells were obtained by washing the human whole blood with saline and centrifuging at 2000 g. The blood cells (240 μL) were added to 900 μL of the aqueous solution of 0.5% sodium polyoxyethylene lauryl sulfate (pH 6.8), which was the anionic surfactant to hemolyze. Subsequently, a 60 μL portion of 320 mg/mL Protin PC10F (from Daiwa Kasei K.K.), which was the protease from *Bacillus* sp., was added to the resulting solution, and was then reacted at 37° C. This solution was reacted with protease for 1, 3, 5, 7, 9, 20, 30, 60, or 120 minutes, subsequent sampling of a part of the solution was performed and a 5 μL portion was injected in the assay apparatus described in (5). Further, the concentrations of fructosyl valylhistidine (FVH), fructosyl valine (FV) and L-lysine (Lys) in the sample were determined simultaneously. The results were shown in FIG. 6.

The detected fructosyl valylhistidine reached to the certain value by the proteolysis for 20 minutes or more, whereas fructosyl valine and L-lysine were detected by the proteolysis for 30 minutes or more, and their concentrations increased with time. From these, under the present condition, the concentration of fructosyl valylhistidine can be determined by the treatment with Protin PC10F for less than 30 minutes without positive interference from fructosyl valine and ε-fructosyl lysine. In the proteolysis by Protin PC10F for 20 minutes, the hemoglobin concentration was determined, the ratio of the detected fructosyl valylhistidine concentration to it was calculated. The ratio was as 4.80%, which was suitable for the HbA1c value 4.3% obtained by the immunoassay.

Example 3

(1) Production of Fructosyl Amino Acid Oxidase Immobilized Column

Firebrick powder (150 mg, 30 to 60 meshes) was thoroughly dried, immersed in 10% solution of γ-aminopropyltriethoxysilane in anhydrous toluene for one hour, and then thoroughly washed with toluene and dried. The aminosilane-modified support was immersed in a 5% aqueous glutaraldehyde solution for one hour, thoroughly washed with distilled water, and followed by the substitution with 100 mM sodium phosphate buffer (pH 7.0). The buffer was removed as far as possible. A solution (200 μL) of fructosyl amino acid oxidase (18 units/mL, from Kikkoman Co.) in 100 mM sodium phosphate buffer (pH 7.0) was contacted with the formylated firebrick powder, and then incubated at 0 to 4° C. for one day for the enzyme immobilization. The support immobilized enzyme was packed into the column (internal diameter: 3.5 mm, length: 30 mm) to give the fructosyl amino acid oxidase-immobilized column.

(2) Production of Electrode for Hydrogen Peroxide

The electrode for hydrogen peroxide was prepared in the same way as described in Example 1 (2).

(3) Production of Electrode for Glucose

The electrode for hydrogen peroxide was produced in the same procedure as described in Example 1 (2). Glucose oxidase (Type II, from Sigma) was dissolved at 100 mg/mL in 100 mM phosphate buffer (pH 6.0). A glucose oxidase solution (100 mg/mL), a bovine serum albumin solution, a glutaraldehyde solution and 100 mM phosphate buffer (pH 6.0) were mixed so that glucose oxidase was 20 mg/mL, bovine serum albumin was 5 mg/mL and glutaraldehyde was 0.2% to use as an enzyme solution for glucose oxidase immobilization. A 5 μL portion of the enzyme solution for glucose oxidase immobilization was expeditiously placed on the electrode for hydrogen peroxide prepared as described above, and dried and cured at 40° C. for 15 minutes. This was used as the electrode for glucose oxidase.

A Ag/AgCl reference electrode was used as the reference electrode, and the conductive piping was used as the counter electrode.

(4) Assay Apparatus

In the assay apparatus shown in FIG. 2, the flow type calorimeter (16), the protease-immobilized column (14) and the first immobilized enzyme column (17) were not disposed, and the electrode for glucose was placed in the electrode for hydrogen peroxide (18), the fructosyl amino acid oxidase-immobilized column in the second immobilized enzyme column (19), and the electrode for hydrogen peroxide in the electrode for hydrogen peroxide (20). The buffer B was pumped out from the buffer tank (24) using the pump (25), and a 100 μL portion of the sample was injected using the valve (4). The injected sample transferred with the flowing buffer B and was carried to the dialysis module (27) in the incubator (13), and only components with low molecular weight in the sample were permeated through the regenerated cellulose membrane with the membrane thickness of 20 μm and molecular weight cut off of 12000 to 14000 to a glucose detection system (18) and a fructosyl amino acid detection system (19, 20). Since the buffer A was pumped out from the buffer tank (1) by the pump (2), the components with low molecular weight in the sample dialyzed in the dialysis module (27) passed through the electrode for glucose (18), the fructosyl amino acid oxidase-immobilized column (19) and the electrode for hydrogen peroxide (20), and hydrogen peroxide from glucose and fructosyl amino acid in the sample was detected.

For the composition of the buffers used in this assay apparatus, the buffer A contained 100 mM phosphoric acid, 50 mM potassium chloride and 1 mM sodium azide; its pH was 8.0, and its flow rate was 0.8 mL/minute. The buffer B contained 50 mM phosphoric acid and 0.1% sodium dodecyl sulfate; its pH was 8.0 and its flow rate was 1.0 mL/minute.

The temperature in the incubator was 37° C.

(5) Substrate Specificity of Fructosyl Amino Acid Oxidase-Immobilized Column

The substrate specificity of fructosyl amino acid oxidase-immobilized column for various fructosyl amino acids, fructosyl peptides, amino acids and sugars was examined using the assay apparatus mentioned in (4) when pH of the buffers was 8.0. The results were shown in Table 3. The values in the Table 3 were normalized to 100 for the response to fructosyl glycine.

The column exhibited large responses to fructosyl glycine and fructosyl valine, and scarcely responded to ε-fructosyl lysine and fructosyl valylhistidine, which was the fructosyl peptide. Among the other amino acids and sugars, extremely small responses to glutamine, methionine and glucose were observed.

This fructosyl amino acid oxidase-immobilized column did not substantially act upon the fructosyl peptide and fructosyl lysine glycated at ε-position.

However, this column responded to glucose. When a large amount of glucose is contained in the sample, it is likely to cause the positive error. The glucose concentration is about 10 mM, whereas the concentration of fructosyl amino acid is about 0.1 mM in normal human blood, that is, glucose is about a 100-fold concentration of the fructosyl amino acid. Thus, it is likely that glucose interferes in the determination as much as fructosyl valine in the blood. Such an interference can be eliminated by the determination of the glucose concentration simultaneously with the fructosyl amino acid concentration and the subtractive operation between them.

TABLE 3

| No. | Sample | Relative response value |
|---|---|---|
| 1 | Fructosyl Glycine | 100.0 |
| 2 | Fructosyl Valine | 30.9 |
| 3 | α, ε-Fructosyl Lysine | 1.1 |
| 4 | Fructosyl Valyl Histidine | 1.3 |
| 5 | Lys | 0.0 |
| 6 | Glu | 0.0 |
| 7 | Gln | 0.2 |
| 8 | Ala | 0.0 |
| 9 | Asp | 0.0 |
| 10 | Phe | 0.0 |
| 11 | Gly | 0.0 |
| 12 | His | 0.0 |
| 13 | Leu | 0.0 |
| 14 | Arg | 0.0 |
| 15 | Ser | 0.0 |
| 16 | Thr | 0.0 |
| 17 | Val | 0.0 |
| 18 | Trp | 0.0 |
| 19 | Met | 0.1 |
| 20 | Asn | 0.0 |
| 21 | Pro | 0.0 |
| 22 | Mannose | 0.0 |
| 23 | Glucose | 0.2 |
| 24 | Fructose | 0.0 |
| 25 | D-sorbitol | 0.0 |
| 26 | Glycerol | 0.0 |
| 27 | Galactose | 0.0 |
| 28 | Xylose | 0.0 |

(6) Simultaneous Determination of Glucose and Fructosyl Valine

Using the assay apparatus mentioned in (4), each 100 μL of 2, 5, 10 mM of glucose and 20, 50, 100 μM of fructosyl valine were injected to obtain the detected values.

Figure 7:
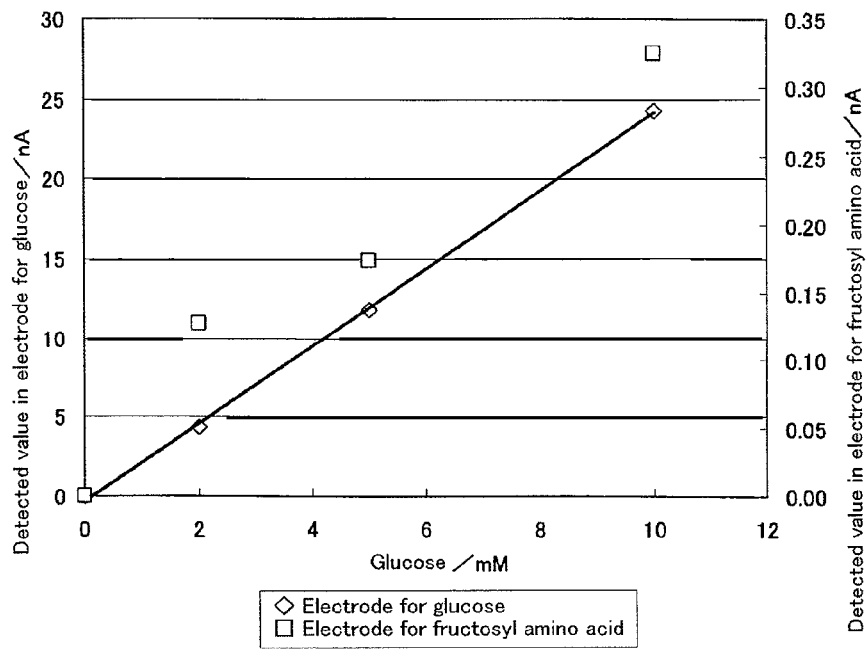
FIG. 7 is a graph showing calibration curves for glucose on an electrode for glucose and a fructosyl amino acid oxidase immobilized enzyme.
Figure 8:
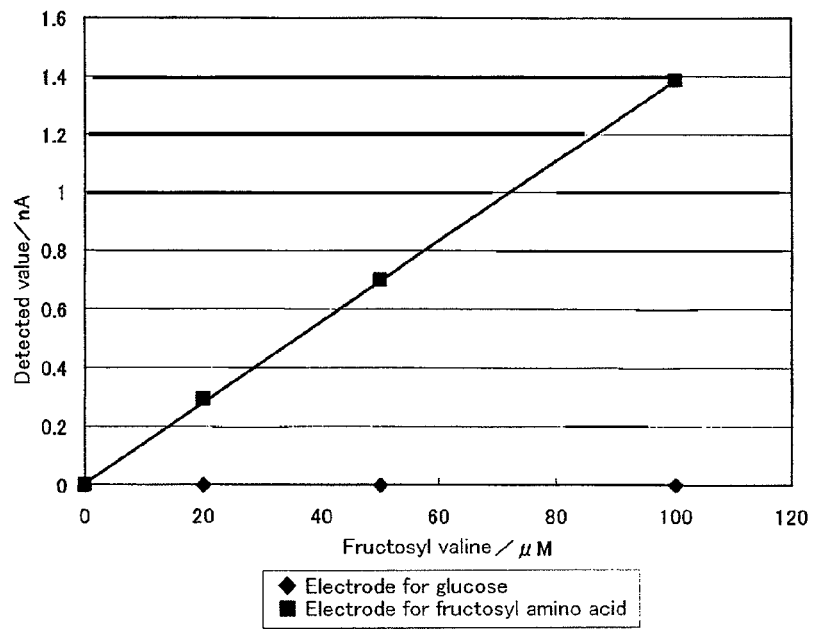
FIG. 8 is a graph showing calibration curves for fructosyl valine on an electrode for glucose and an immobilized enzyme of a fructosyl amino acid oxidase.

The detected values for glucose in the electrode for glucose and the electrode for the fructosyl amino acid were shown in FIG. 7. The detected values for fructosyl valine in the electrode for glucose and the electrode for the fructosyl amino acid were shown in FIG. 8. The calibration curves shown below were obtained. Y, X and r represent the detected value, the concentration in the sample and the correlation coefficient, respectively.

Electrode for Glucose

Calibration curve for glucose: $Y(nA)=2.44\times(mM)-0.25, r=0.9998$

Calibration curve for fructosyl valine: $Y(nA)=0.00\times(\mu M)-0.00$

Electrode for Fructosyl Amino Acid

Calibration curve for glucose: $Y(nA)=0.030\times(mM)+0.029, r=0.9778$

Calibration curve for fructosyl valine: $Y(nA)=0.014\times(\mu M)+0.007, r=0.9999$ Using this assay apparatus, a mixture standard solution of 5 mM glucose and 80 µM fructosyl valine was measured, and a response value of 11.97 nA in the electrode for glucose and a response value of 1.29 nA in the electrode for the fructosyl amino acid were obtained.

For the glucose concentration $X_1$, $X_1=5.00$ mM could be obtained by the formula $X_1=(Y_1-b_{11})/a_{11}$. For the concentration of fructosyl valine $X_2$, $X_2=80$ µM could be obtained by the formula $X_2=[a_{11}\times(Y_2-b_{21}-b_{22})-a_{21}\times(Y_1-b_{11})]/(a_{11}\times a_{22})$.

Comparative Example 2

The sample containing glucose and fructosyl valine was measured using only the electrode for the fructosyl amino acid in the same way as described in Example 3 (6).

(1) Production of Fructosyl Amino Acid Oxidase-Immobilized Column

The fructosyl amino acid oxidase-immobilized column was produced in the same way as described in Example 3 (1).

(2) Production of Electrode for Hydrogen Peroxide

The electrode for hydrogen peroxide was produced in the same way as described in Example 1 (2).

(3) Assay Apparatus

The measurement was performed by the assay apparatus shown in FIG. 2 in the same way as described in Example 3 (4). The flow type calorimeter (16), the protease-immobilized column (14), the first enzyme immobilized column (17) and the electrode for hydrogen peroxide (18) were not disposed, and the fructosyl amino acid oxidase-immobilized column was placed in the second immobilized enzyme column (19), and the electrode for hydrogen peroxide in the electrode for hydrogen peroxide (20). The sample (100 µL) was injected by the valve.

The conditions, e.g., the composition and the flow rate of the buffer used in this apparatus and the temperature in the incubator were the same as those in Example 3.

(4) Assay of Mixture Standard Solution of Glucose and Fructosyl Valine

Using the assay apparatus mentioned in (3), a 100 µL portion of 20, 50, 100 µM of fructosyl valine was injected to obtain the detected values. The calibration curve for fructosyl valine was $Y(nA)=0.014\times(\mu M)+0.007, r=0.9999$.

Y, X and r represent the detected value, the concentration in the sample and the correlation coefficient, respectively.

Using this assay apparatus, the mixture standard solution of 5 mM glucose and 80 µM fructosyl valine was measured, and the response value of 1.28 nA was obtained. Thus, the concentration $X_2$ of fructosyl valine was calculated to be 92.3 µM from the formula $X_2=(Y_2-b_{22})/a_{22}$, but this value contained the positive error due to glucose.

Example 4

(1) Production of Fructosyl Peptide Oxidase-Immobilized Column

In the same way as described in Example 1 (1), 150 mg of firebrick powder (30 to 60 meshes) was formylated. The solution (200 µL) of fructosyl peptide oxidase (140 units/mL, from Kikkoman Co.) in 100 mM sodium phosphate buffer (pH 7.0) was contacted with the formylated firebrick powder, and then incubated at 0 to 4° C. for one day for the enzyme immobilization. The support immobilized enzyme was packed into the column (internal diameter: 3.5 mm, length: 30 mm) to give the fructosyl peptide oxidase immobilized column.

(2) Production of Electrode for Hydrogen Peroxide

The electrode for hydrogen peroxide was produced in the same way as described in Example 1 (2).

(3) Production of Electrode for Glucose

The electrode for glucose was produced in the same way as described in Example 3 (3).

(4) Assay Apparatus

In the assay apparatus shown in FIG. 1, the protease-immobilized column (14), the flow type calorimeter (16) and the first immobilized enzyme column (17) were not disposed, and the electrode for glucose was placed in the electrode for hydrogen peroxide (18), the fructosyl peptide oxidase-immobilized column in the second immobilized enzyme column (19), and the electrode for hydrogen peroxide in the electrode for hydrogen peroxide (20). The buffer A was pumped out from the buffer tank (1) by the pump (2), and a 5 µL portion of the sample was injected using the valve (4). The injected sample transferred with the flowing buffer A, passed through the mixing coil (15) in the incubator (13), and thus the sample temperature was adjusted and the sample was mixed with the buffer. And then the sample passed through the downstream electrode for glucose (18), fructosyl peptide oxidase-immobilized column (19) and an electrode for hydrogen peroxide (20), hydrogen peroxide was produced from fructosyl valyl-histidine in the sample, and the change of the current was detected.

The composition of the buffer A for the assay apparatus contained 100 mM phosphoric acid, 50 mM potassium chloride and 1 mM sodium azide, and its pH was 7.0.

The flow rate of the buffer was 1.0 mL/minute, and the temperature in the incubator was 30° C.

(5) Substrate Specificity of Fructosyl Peptide Oxidase-Immobilized Column

On fructosyl peptide oxidase-immobilized column, the substrate specificity for various fructosyl amino acids, fructosyl peptides, amino acids and sugars was examined using the assay apparatus mentioned in (4) when pH of the buffer A was 7.0. The results were shown in Table 4. In the Table 4, the relative values were normalized to 100 for the response to fructosyl valine.

The column was specific for fructosyl valylhistidine and fructosyl valine, scarcely responded to α, ε-fructosyl lysine and did not respond to the other amino acids and sugars at all. Therefore, in the determination of glycohemoglobin, it is unlikely that the positive error due to the amino acids or blood glucose occurs when the digestion of glycohemoglobin by protease progresses considerably. Thus, it is not necessary to correct them.

TABLE 4

| No. | Sample name | Relative response value |
|---|---|---|
| 1 | Fructosyl Glycine | 56.3 |
| 2 | Fructosyl Valine | 100.0 |
| 3 | α, ε-Fructosyl Lysine | 9.9 |
| 4 | Fructosyl Valyl Histidine | 86.8 |
| 5 | Lys | 0.0 |
| 6 | Glu | 0.0 |
| 7 | Gln | 0.0 |
| 8 | Ala | 0.0 |
| 9 | Asp | 0.0 |
| 10 | Phe | 0.0 |
| 11 | Gly | 0.0 |
| 12 | His | 0.0 |
| 13 | Leu | 0.0 |
| 14 | Arg | 0.0 |
| 15 | Ser | 0.0 |
| 16 | Thr | 0.0 |
| 17 | Val | 0.0 |
| 18 | Trp | 0.0 |
| 19 | Met | 0.0 |
| 20 | Asn | 0.0 |
| 21 | Pro | 0.0 |
| 22 | Mannose | 0.0 |
| 23 | Glucose | 0.0 |
| 24 | Fructose | 0.0 |
| 25 | D-sorbitol | 0.0 |
| 26 | Glycerol | 0.0 |
| 27 | Galactose | 0.0 |
| 28 | Xylose | 0.0 |

(6) Simultaneous Determination of Glucose and Fructosyl Valine

Utilizing the assay apparatus mentioned in (4), each 5 μL of 2, 5, 10 mM glucose and 10, 20, 50, 100 μM fructosyl valine was injected, and the detected values were obtained.

Each calibration curve was shown below. Y, X and r represent the detected value, the concentration in the sample and the correlation coefficient, respectively.

Electrode for Glucose

Calibration curve for glucose: $Y(nA)=6.74 \times (mM)-0.28, r=1.0000$

Calibration curve for fructosyl valine: $Y(nA)=0.00 \times (\mu M)-0.00$

Electrode for Fructosyl Peptide

Calibration curve for glucose: $Y(nA)=0.00 \times (mM)+0.00$

Calibration curve for fructosyl valine: $Y(nA)=0.035 \times (\mu M)+0.087, r=0.9992$ Using this assay apparatus, the mixture standard solution of 5 mM glucose and 80 μM fructosyl valine was measured, and the response value of 34.1 nA in the electrode for glucose and the response value of 2.87 nA in the electrode for the fructosyl peptide were obtained.

For the glucose concentration $X_1$, $X_1=5.01$ mM could be obtained by the formula $X_1=(Y_1-b_{11})/a_{11}$. For the concentration of fructosyl valine $X_2$, $X_2=80.0$ μM could be obtained by the formula $X_2=(Y_2-b_{22})/a_{22}$.

On the fructosyl peptide oxidase-immobilized column, because the column did not respond to glucose, the concentration of the fructosyl amino acid or fructosyl peptide could be precisely determined without the subtractive operation.

Example 5

(1) Production of Fructosyl Amino Acid Oxidase-Immobilized Column

The fructosyl amino acid oxidase-immobilized column was produced in the same way as described in Example 3 (1).

(2) Production of Electrode for Hydrogen Peroxide

The electrode for hydrogen peroxide was produced in the same way as described in Example 1.

(3) Assay Apparatus 1

The assay apparatuses shown in FIGS. 1 and 2 were used in the same way as described in Example 1 and Example 3.

FIG. 1 was the flow type assay apparatus with one flow path. The buffer A was pumped out from the buffer tank (1) using the pump (2), and a 5 μL portion of the sample was injected using the valve (4). The fructosyl amino acid oxidase-immobilized column was placed in the first immobilized enzyme column (17) and the electrode for hydrogen peroxide was placed downstream. The second immobilized enzyme column (19), the second electrode for hydrogen peroxide (20), the protease-immobilized column (14) and the flow type calorimeter (16) were not disposed. The injected sample transferred with the flowing buffer, passed through the mixing coil (15) in the incubator (13), and thus the sample temperature was adjusted and the sample was mixed with the buffer. The sample passed through the fructosyl amino acid oxidase-immobilized column (17) and the electrode for hydrogen peroxide (18), hydrogen peroxide was produced from fructosyl valine in the sample, and the change of the current was detected.

The composition of the buffer for this assay apparatus contained 100 mM phosphoric acid, 50 mM potassium chloride and 1 mM sodium azide, and its pH was 8.0.

The flow rate of the buffer was 1.0 mL/minute, and the temperature in the incubator was 37° C.

(4) Assay Apparatus 2

As described in Example 3, the assay apparatus with the dialysis module shown in FIG. 2 was used.

FIG. 2 was the flow type assay apparatus for fructosyl amino acid with the dialysis module. The buffer B was pumped out from the buffer tank (24) using the pump (25), and a 100 μL portion of the sample was injected using the valve (4). The protease-immobilized enzyme column (14), the second immobilized enzyme column (19), the electrode for hydrogen peroxide (20) and the flow type calorimeter (16) were not disposed. The fructosyl amino acid oxidase-immobilized column was placed in the first immobilized enzyme column (17). The injected sample transferred with the flowing buffer B, was carried to the dialysis module (27) in the incubator (13), and only the components with low molecular weight in the sample were permeated through the regenerated cellulose membrane with the membrane thickness of 20 μm and molecular weight cut off of 12000 to 14000 to a detection system (17, 18) of the fructosyl amino acid. Since the buffer A was pumped out from the buffer tank (1) by the pump (2), the components with low molecular weight in the sample dialyzed by the dialysis module passed through the fructosyl amino acid oxidase-immobilized column (17) and the electrode for hydrogen peroxide (18), and hydrogen peroxide produced from the fructosyl amino acid in the sample was detected.

For the composition of the buffers used in this assay apparatus, the buffer A contained 100 mM phosphoric acid, 50 mM potassium chloride and 1 mM sodium azide; its pH was 8.0, and its flow rate was 0.8 mL/minute. The buffer B contained 50 mM phosphoric acid and 0.1% sodium dodecyl sulfate; its pH was 8.0 and its flow rate was 0.8 mL/minute.

The temperature in the incubator was 37° C.

(5) Characteristics of Fructosyl Amino Acid Oxidase-Immobilized Column

Figure 9:
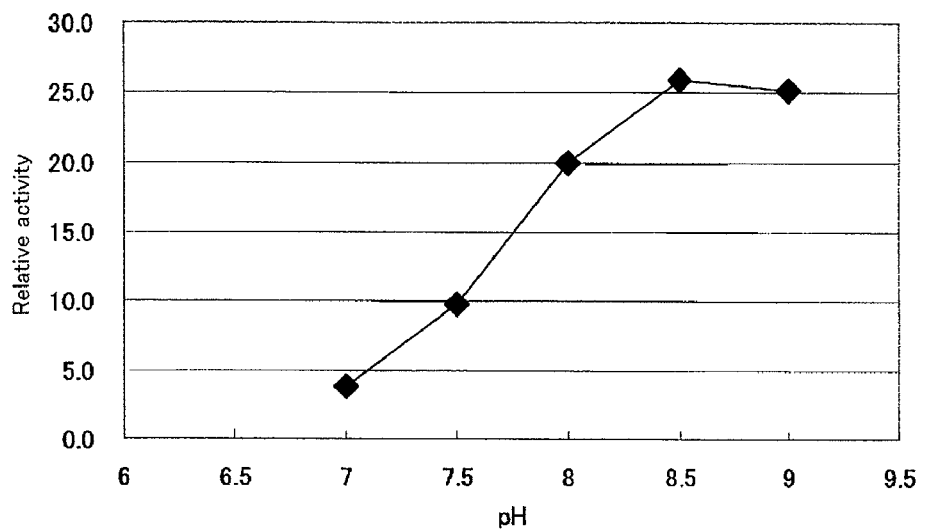
FIG. 9 is a graph showing pH profile of an immobilized enzyme.

Using the assay apparatus 1 mentioned in (3), a 5 μL portion of fructosyl glycine was injected, and the characteristics of the fructosyl amino acid oxidase-immobilized column was examined. The results were shown below.
pH profile
When pH in the buffer was 7.0, 7.5, 8.0, 8.5 or 9.0, the activity in the oxidation of fructosyl glycine was measured. The results were shown in FIG. 9. The high activity was observed at pH 8.0 to 9.0.
Substrate Specificity
The substrate specificity on the fructosyl amino acid oxidase-immobilized column was shown in Table 5.

TABLE 5

| | Sample name | Concentration | Relative activity (%) |
|---|---|---|---|
| 1 | Fructosyl glycine | 0.1 mM | 100.0 |
| 2 | Fructosyl valine | 0.1 mM | 32.0 |
| 3 | α, ε-Fructosyl lysine | 0.1 mM | 5.0 |
| 4 | Ala | 10 mM | 0.0 |
| 5 | Asp | 10 mM | 0.0 |
| 6 | Glu | 10 mM | 0.0 |
| 7 | Phe | 10 mM | 0.0 |
| 8 | Gly | 10 mM | 0.0 |
| 9 | His | 10 mM | 0.0 |
| 10 | Lys | 10 mM | 41.0 |
| 11 | Leu | 10 mM | 0.0 |
| 12 | Met | 10 mM | 8.0 |
| 13 | Asn | 10 mM | 0.0 |
| 14 | Pro | 10 mM | 2.0 |
| 15 | Gln | 10 mM | 6.0 |
| 16 | Arg | 10 mM | 1.0 |
| 17 | Ser | 10 mM | 0.0 |
| 18 | Thr | 10 mM | 2.0 |
| 19 | Val | 10 mM | 0.0 |
| 20 | Trp | 10 mM | 13.0 |
| 21 | Cys | 10 mM | 507.0 |
| 22 | Glucose | 10 mM | 9.0 |
| 23 | Fructose | 10 mM | 1.0 |
| 24 | D-Sorbitol | 10 mM | 0.0 |
| 25 | Glycerol | 10 mM | 0.0 |
| 26 | Galactose | 10 mM | 0.0 |

TABLE 5-continued

| | Sample name | Concentration | Relative activity (%) |
|---|---|---|---|
| 27 | Xylose | 10 mM | 0.0 |
| 28 | Mannose | 10 mM | 0.0 |

Stability

Under the condition of the buffer at pH 8.0, the flow rate of the buffer at 1.0 mL/minute and the incubator temperature at 37° C., the fructosyl amino acid oxidase-immobilized column kept its initial activity for one month or more, and was stable.

The fructosyl amino acid oxidase-immobilized column did not act upon ε-fructosyl lysine substantially, and selectively acted upon fructosyl glycine and fructosyl valine glycated at position α. The optimal pH was in the alkaline region. Thus, it is desirable that the protease used for the determination of the fructosyl amino acid in the protein has the high activity in the alkaline region.

(6) Separation of Components with Low Molecular Weight Through Semipermeable Membrane When the amino acid and the fructosyl amino acid produced by the proteolysis of human hemoglobin were determined using the electrode for the amino acid or the fructosyl amino acid oxidase-immobilized enzyme column and the electrode for hydrogen peroxide, the separation of only components with low molecular weight by a semipermeable membrane after the proteolysis enabled to determine the amino acid and the fructosyl amino acid in human hemoglobin with good reproducibility.

(7) Proteolysis of Human Hemoglobin

The fructosyl amino acid oxidase-immobilized column with the optimum in the alkaline region was used for the determination of the fructosyl amino acid produced by the proteolysis of human hemoglobin. Thus, the alkaline protease, Umamizyme G (from Amano Enzyme Inc.) with the high activity in the alkaline region from Aspergillus oryzae was used.

A protease treatment solution was prepared by weighing human hemoglobin (from Sigma), dissolving it in 20 mM phosphate buffer pH 8.0 containing 2% sodium dodecyl sulfate and adding 1 mg/mL of Umamizyme G. The human hemoglobin concentration in the protease treatment solution was 30 mg/mL.

The protease treatment solution prepared in this way was reacted at 37° C. for 8, 17, 25, 33, 42 or 51 minutes, a 100 μL portion of them was injected in the assay apparatus mentioned in (4), and the concentration of fructosyl valine in the sample was determined.

Figure 10:
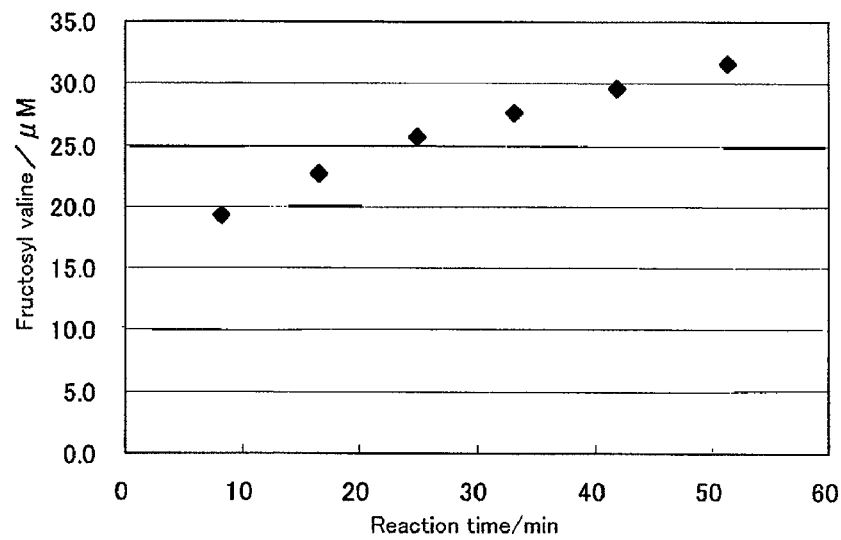
FIG. 10 is a graph showing a time course of proteolysis in a solution.

The concentration of fructosyl valine at each reaction time was changed as shown in FIG. 10. When human hemoglobin was not treated with protease, fructosyl valine was not detected at all, and it was suggested that fructosyl valine was liberated from hemoglobin by the proteolysis for the given time. This protease acted upon human hemoglobin efficiently.

Comparative Example 3

The proteolysis of human hemoglobin was examined using the proteases which were different from Umamizyme in origins and optimal pH.

The used proteases were Umamizyme G (*Aspergillus oryzae*), Protease A "Amano" G (*Aspergillus oryzae*), Protease N "Amano" G (*Bacillus subtilis*), Bromelain F (*Ananas comosus* M), Peptidase R (*Rhizopus oryzae*) and Protease P "Amano" 3G (*Aspergillus melleus*) from Amano Enzyme Inc., Proteinase K (*Tritirachium album*) and Protease XIV (*Streptomyces griseus*) from Sigma-Aldrich Co., and Sumizyme MP (*Aspergillus* sp.) from Shin-Nihon Chemical Co., Ltd.

In the same way as described in Example 5 (6), the protease treatment solution was prepared using human hemoglobin and 1 mg/mL of the above each protease, and after the proteolysis at 37° C. for 30 minutes, a 100 μL portion of them was injected into the assay apparatus 2 described in Example 5 (4). The results were shown in Table 6. In the Table 6, result "A" represents the detected value of 40 pA or more of the fructosyl amino acid, result "B" represents the detected value of about 25 pA, and result "C" represents the detected value of less than 20 pA.

TABLE 6

| Protease | Origin | Optimal pH | Result | Remarks |
|---|---|---|---|---|
| A | *Aspergillus oryzae* | Alkaline | A | Umamizyme G |
| B | *Aspergillus oryzae* | Neutral | B | Protease A "Amano" G |
| C | *Bacillus subtilis* | Neutral | C | Protease N "Amano" G |
| D | *Ananas comosus* M. | Neutral | C | Bromelain F |
| E | *Rhizopus oryzae* | Neutral | C | Peptidase R |
| F | *Tritirachium album* | | C | Proteinase K |
| G | *Aspergillus* sp. | | C | Sumizyme MP |
| H | *Streptomyces* sp. | | C | Protease XIV |

The large detected values were observed in the proteases from *Aspergillus oryzae*, but the fructosyl amino acid was not detected in the other enzymes. It is suggested that the protease from *Aspergillus oryzae* is effective for the proteolysis of human hemoglobin. Furthermore, among the proteases from *Aspergillus oryzae*, the protease with the alkaline optimal pH gave the larger detected value than that with the neutral optimal pH. Thus, it was found that the protease from *Aspergillus oryzae* with the alkaline optimal pH was most appropriate for the proteolysis of human hemoglobin.

Example 6

As shown in Example 5, the use of the protease from *Aspergillus oryzae* enabled the proteolysis of human hemoglobin and the determination of the amino acid and the fructosyl amino acid from human hemoglobin using the assay apparatus with the semipermeable membrane. Furthermore, in order to simplify the treatment and shorten the analytical time, the column immobilized this protease onto the support with high density was used. Details were shown below.

(1) Production of Fructosyl Amino Acid Oxidase-Immobilized Column

The fructosyl amino acid oxidase (from Kikkoman Co.)— immobilized column was produced in the same way as described in Example 2 (2).

(2) Production of Lysine Oxidase-Immobilized Column

The lysine oxidase-immobilized column was produced in the same way as described in Example 2.

(3) Production of Umamizyme G-Immobilized Column

Toyonite 200 (300 mg, average diameter of particles: 170 μm, from Toyo Denka Kogyo Co., Ltd.) was immersed in 10% solution of γ-aminopropyltriethoxysilane in 20% ethanol for one hour, washed thoroughly with distilled water, and dried. The aminosilane-modified support in this way was immersed in 5% glutaraldehyde for 1 hour, then washed thoroughly with distilled water, and followed by the substitution with 100 mM sodium phosphate buffer (pH 7.0), and this buffer was removed as far as possible. Umamizyme G solution (800 μL, 100 mg/mL, from Amano Enzyme Inc.) in 100 mM sodium phosphate buffer (pH 7.0) was contacted with the formylated Toyonite 200, and then incubated for one day at 0 to 4° C. for the enzyme immobilization. The support immobilized enzyme was packed into the column (internal diameter: 3.5 mm, length: 30 mm) to give the Umamizyme G-immobilized column.

(4) Production of Electrode for Hydrogen Peroxide

The electrode for hydrogen peroxide was produced in the same way as described in Example 5.

(5) Assay Apparatus

The Umamizyme G-immobilized column, the fructosyl amino acid oxidase-immobilized column and the lysine oxidase-immobilized column were incorporated in the protease-immobilized enzyme column (14), the first immobilized enzyme column (17) and the second immobilized enzyme column (18) shown in FIG. 2, respectively, to make the flow type assay apparatus capable of the simultaneous determination of the fructosyl amino acid and L-lysine. The buffer B was pumped out from the buffer tank (24) by the pump (25), and a 100 μL portion of the sample was injected using the valve (4). The injected sample transferred with the flowing buffer B, and was carried to the Umamizyme G-immobilized column in the incubator (13) to produce the fructosyl amino acid and the amino acids by the action of Umamizyme G. The sample treated by Umamizyme G was carried to the further downstream dialysis module (27) by the flowing buffer B, and only the components with low molecular weight in the sample permeated through the regenerated cellulose membrane with the membrane thickness of 20 μm and molecular weight cut off of 12,000 to 14,000 to the detection systems of the fructosyl amino acid and the amino acid. Since the buffer A was pumped out from the buffer tank (1) by the pump (2), the components with low molecular weight in the sample dialyzed in the dialysis module (27) passed through the fructosyl amino acid oxidase-immobilized column (17) and the electrode for hydrogen peroxide, and hydrogen peroxide from the fructosyl amino acid in the sample was detected. Subsequently, the buffer containing the sample passed through the detection system (17, 18) of the fructosyl amino acid, and then passed through the lysine oxidase-immobilized column (19) and the electrode for hydrogen peroxide (20), and hydrogen peroxide from lysine in the sample was detected.

For the composition of the buffers used in this assay apparatus, the buffer A contained 100 mM phosphoric acid, 50 mM potassium chloride and 1 mM sodium azide; its pH was 8.0, and its flow rate was 0.8 mL/minute. The buffer B contained 50 mM phosphoric acid and 0.1% sodium dodecyl sulfate; its pH was 8.0 and its flow rate was 0.8 mL/minute.

The temperature in the incubator was 37° C.

(6) Determination of Fructosyl Amino Acid and Amino Acid in Human Hemoglobin

A human hemoglobin solution (100 μL) was injected in the assay apparatus mentioned in (5), and the concentrations of fructosyl valine and lysine were simultaneously determined.

The human hemoglobin solution was prepared by weighing human hemoglobin (from Sigma) so that the hemoglobin concentration was 30 mg/mL, and thoroughly dissolving it in 20 mM phosphate buffer (pH 8.0) containing 2% sodium dodecyl sulfate.

The concentrations of fructosyl valine and lysine in the solution of 30 mg/mL human hemoglobin were determined in the assay apparatus mentioned in (5). As a result, the fructosyl valine concentration was 15.1 μM and the lysine concentration was 12.6 μM.

About 20 minutes of the reaction time was required for production of about 15 μM of fructosyl valine described in Example 1 used the enzyme solution. However, in the present assay apparatus, about 15 μM of fructosyl valine could be produced at the time (about 10 seconds) contacting the Umamizyme G-immobilized column with the sample. By the immobilization of Umamizyme G with high density enabled to digest efficiently human hemoglobin.

Industrial Applicability

The present invention provides the simple and precise determination of stable glycohemoglobin in the blood sample, and the contamination in the assay apparatus can be avoided. Stable glycohemoglobin and glucose in the blood sample can be simultaneously determined simply and precisely. Therefore, it is possible to easily perform a diabetes examination.

The invention claimed is:

1. An apparatus for assaying glycohemoglobin characterized by having:
   an immobilized enzyme (17) which is either immobilized fructosyl peptide oxidase which acts upon fructosyl valylhistidine or immobilized fructosyl amino acid oxidase which acts upon fructosyl valine and
   an electrochemical detector (18) to detect electroactive components which are produced/consumed by a reaction which said immobilized oxidase catalyzes, and
   comprising machineries (4, 5, 7) to contact a sample containing glycohemoglobin with a protease for a given time and inject a part thereof.

2. An apparatus for assaying glycohemoglobin comprising:
   an immobilized enzyme (17) which is either immobilized fructosyl peptide oxidase which acts upon fructosyl valylhistidine or immobilized fructosyl amino acid oxidase which acts upon fructosyl valine,
   an electrochemical detector (18) to detect electroactive components which are produced/consumed by a reaction which said immobilized oxidase catalyzes and
   machineries (4, 5, 7) to inject a sample containing glycohemoglobin, and
   characterized by comprising a column shaped reactor (14) in which a protease has been immobilized downstream of the machinery to inject the sample.

3. The apparatus for assaying glycohemoglobin as defined in claim 1 or 2 characterized in that when fructosyl peptide oxidase, which acts upon fructosyl valylhistidine, is immobilized to use, the protease contacting with the sample containing glycohemoglobin for a certain time is a neutral or acidic protease generated by *Bacillus subtilis* or variants thereof.

4. The apparatus for assaying glycohemoglobin as defined in claim 1 or 2 characterized in that when fructosyl amino acid oxidase, which acts upon fructosyl valine, is immobilized to use, the protease contacting the sample containing glycohemoglobin for a certain time is an alkaline protease generated by *Aspergillus oryzae* or variants thereof.

5. An apparatus for assaying glycohemoglobin comprising:
   an immobilized enzyme (17) which is either immobilized fructosyl peptide oxidase which acts upon fructosyl valylhistidine or immobilized fructosyl amino acid oxidase which acts upon fructosyl valine,
   an electrochemical detector (18) to detect electroactive components which are produced/consumed by a reaction which said immobilized oxidase catalyzes and
   machineries (4, 5, 7) to inject a sample containing glycohemoglobin, and
   characterized by comprising systems to calculate a hemoglobin amount from an absorbance of the sample and calculate the proportion of total hemoglobin that is glycohemoglobin from the hemoglobin amount and a fructosyl peptide amount or a fructosyl amino acid amount in or downstream of the machineries (4, 5, 7) to inject the sample.

6. An apparatus for assaying glucose and glycohemoglobin characterized by comprising an immobilized enzyme which catalyzes an oxidation of glucose and a system to detect electroactive components which are produced/consumed by the oxidation of glucose;
   further comprising a system to detect electroactive components which are produced/consumed due to an oxidation of fructosyl valylhistidine by an immobilized fructosyl peptide oxidase and a system to detect total hemoglobin; and
   comprising a first arithmetic system for determining the proportion of total hemoglobin that is glycohemoglobin, based on the detection of fructosyl valylhistidine and the detection of total hemoglobin, and a second arithmetic system to correct glucose in whole blood into glucose in plasma based on detection results of glucose in whole blood and hemoglobin.

7. An apparatus for assaying glucose and glycohemoglobin characterized by comprising:
   an immobilized enzyme which catalyzes an oxidation of glucose;
   a system to detect electroactive components which are produced/consumed by the oxidation of glucose;
   an immobilized fructosyl amino acid oxidase which acts upon fructosyl valine or an immobilized fructosyl peptide oxidase which acts upon fructosyl valylhistidine;
   a system to detect electroactive components which are produced/consumed due to an oxidation of fructosyl amino acid or fructosyl peptide;
   a system to detect total hemoglobin;
   a first arithmetic system to obtain an amount of fructosyl valylhistidine or fructosyl valine with eliminating interference from glucose in the sample based on a detection result of glucose and fructosyl valylhistidine in the sample or a detection result of glucose and fructosyl valine in the sample;

a second arithmetic system to obtain a ratio of glycohemoglobin based on said amounts of fructosyl valylhistidine and hemoglobin or fructosyl valine and hemoglobin and the detection result of hemoglobin; and a third arithmetic system to correct glucose in whole blood into glucose in plasma based on the detection results of glucose in whole blood and hemoglobin.

8. A method for assaying glycohemoglobin comprising:

dispersing a whole blood sample in a solution containing a surfactant to hemolyze;

contacting a protease with the hemolyzate for a given time; and determining a hemoglobin concentration by measuring an absorbance of a reaction solution of said protease, as well as contacting a part of the reaction solution with an immobilized enzyme which is either immobilized fructosyl peptide oxidase which acts upon fructosyl valylhistidine or immobilized fructosyl amino acid oxidase which acts upon fructosyl valine, and electrochemical detection of electroactive components which are produced/consumed by a reaction which said immobilized oxidase catalyzes.

9. The method for assaying glycohemoglobin as defined in claim 8 characterized in that the surfactant is anionic with sulfone group.

10. A method for assaying glucose and glycohemoglobin in a sample comprising:

a step of an electrochemical detection of a glucose concentration in the sample using an immobilized enzyme which catalyzes an oxidation of glucose and a system to detect electroactive components which are produced/consumed by the oxidation of glucose;

a step of an electrochemical detection of fructosyl valylhistidine in the sample using an immobilized fructosyl peptide oxidase which acts upon fructosyl valylhistidine, and a system to detect electroactive components which are produced/consumed by an oxidation of fructosyl peptide;

a step of detection of total hemoglobin in the sample using a system to detect total hemoglobin;

a step of determining the proportion of total hemoglobin that is HbA1c using a first arithmetic system based on the detection of fructosyl valylhistidine and hemoglobin; and a step of correcting glucose in whole blood/blood cell into glucose in plasma by a second arithmetic system based on the detection results of glucose in whole blood/blood cell and hemoglobin.

11. A method for assaying glucose and glycohemoglobin in a sample comprising:

a step of an electrochemical detection of a glucose concentration in the sample using an immobilized enzyme which catalyzes an oxidation of glucose and a system to detect electroactive components which are produced/consumed by the oxidation of glucose;

a step of an electrochemical detection of fructosyl L-valine or fructosyl valylhistidine in the sample using an immobilized fructosyl amino acid oxidase which acts upon fructosyl L-valine or an immobilized fructosyl peptide oxidase which acts upon fructosyl valylhistidine, and a system to detect electroactive components which are produced/consumed by an oxidation of fructosyl amino acid or fructosyl peptide;

a step of detection of total hemoglobin in the sample using a system to detect total hemoglobin;

a step of correcting glucose in whole blood/blood cell into glucose in plasma by a first arithmetic system based on the detection results of glucose in whole blood/blood cell and hemoglobin;

a step of obtaining an amount of fructosyl L-valine or fructosyl valylhistidine with eliminating an interference from glucose in the sample by a second arithmetic system based on the detection results of glucose and fructosyl L-valine in the sample or the detection results of glucose and fructosyl valylhistidine in the sample; and determining the proportion of total hemoglobin that is HbA1c using a third arithmetic system based on the obtained amount and the detection of hemoglobin.

* * * * *